(12) United States Patent
Ni et al.

(10) Patent No.: US 7,022,683 B1
(45) Date of Patent: *Apr. 4, 2006

(54) PHARMACOLOGICAL COMPOSITIONS COMPRISING PECTINS HAVING HIGH MOLECULAR WEIGHTS AND LOW DEGREES OF METHOXYLATION

(75) Inventors: Yawei Ni, College Station, TX (US); Kenneth M. Yates, Grand Prairie, TX (US); Ryszard Zarzycki, Dallas, TX (US)

(73) Assignee: Carrington Laboratories, Inc., Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/325,610

(22) Filed: Jun. 3, 1999

Related U.S. Application Data

(63) Continuation of application No. 09/078,204, filed on May 13, 1998, now Pat. No. 5,929,051.

(51) Int. Cl.
*A61K 31/725* (2006.01)
*C08B 37/06* (2006.01)

(52) U.S. Cl. .................... 514/54; 536/2; 536/123; 536/123.1; 424/461; 424/479; 424/402; 424/439; 426/50; 426/577

(58) Field of Classification Search ................. 424/461, 424/479, 402, 439; 514/54; 536/2, 123, 536/123.1; 426/50, 577
See application file for complete search history.

(56) References Cited

U.S. PATENT DOCUMENTS

| 3,982,003 | A | 9/1976 | Mitchell et al. | |
|---|---|---|---|---|
| 5,071,644 | A | 12/1991 | Viegas et al. | |
| 5,122,597 | A | 6/1992 | Barritault et al. | 530/399 |
| 5,130,418 | A | 7/1992 | Thompson | 530/399 |
| 5,147,648 | A | 9/1992 | Bannert | |
| 5,191,067 | A | 3/1993 | Lappi et al. | 530/399 |
| 5,217,954 | A | 6/1993 | Foster et al. | 514/12 |
| 5,238,917 | A | 8/1993 | Fujii et al. | |
| 5,310,883 | A | 5/1994 | Seddon et al. | 530/399 |
| 5,318,780 | A | 6/1994 | Viegas et al. | |
| 5,356,630 | A | 10/1994 | Laurencin et al. | 424/426 |
| 5,422,340 | A | 6/1995 | Ammann et al. | 514/12 |
| 5,453,492 | A | 9/1995 | Butzow et al. | 530/413 |
| 5,464,815 | A | 11/1995 | Chamow et al. | 514/8 |
| 5,505,966 | A | 4/1996 | Edman et al. | |
| 5,514,652 | A | 5/1996 | Watanuki et al. | 514/12 |
| 5,552,528 | A | 9/1996 | Burgess et al. | 530/399 |
| 5,576,288 | A | 11/1996 | Lappi et al. | 514/2 |
| 5,587,175 | A | 12/1996 | Viegas et al. | |
| 5,589,451 | A | 12/1996 | Wilson | 512/2 |

(Continued)

FOREIGN PATENT DOCUMENTS

JP 06205687 * 7/1994

(Continued)

OTHER PUBLICATIONS

Munjeri et al. "In vivo behavior of hydrogel beads based on amidated beads", Drug Delivery, vol. 5(4): 239-241, 1998.*

(Continued)

*Primary Examiner*—James O. Wilson
*Assistant Examiner*—Devesh Khare
(74) *Attorney, Agent, or Firm*—Needle & Rosenberg, P.C.

(57) ABSTRACT

The inventions disclosed herein relate to compositions for the sustained release of pharmacological agents comprising pectins having a combination of both a high molecular weight and a low degree of methoxylation.

26 Claims, 5 Drawing Sheets

U.S. PATENT DOCUMENTS

| | | | |
|---|---|---|---|
| 5,604,204 A | 2/1997 | Ammann et al. | 514/12 |
| 5,612,211 A | 3/1997 | Wilson et al. | 435/378 |
| 5,614,496 A | 3/1997 | Dunstan et al. | 514/12 |
| 5,656,587 A | 8/1997 | Sporn et al. | 514/2 |
| 5,656,598 A | 8/1997 | Dunstan et al. | 514/12 |
| 5,665,870 A | 9/1997 | Rubin et al. | 530/412 |
| 5,693,775 A | 12/1997 | Nathans et al. | 536/23.1 |
| 5,703,047 A | 12/1997 | Wilson | 514/12 |
| 5,714,458 A | 2/1998 | Adami et al. | 514/2 |
| 5,753,622 A | 5/1998 | Buret et al. | 514/12 |
| 5,849,327 A * | 12/1998 | Berliner et al. | 424/463 |
| 5,929,051 A * | 7/1999 | Ni et al. | 514/54 |
| 5,958,443 A | 9/1999 | Viegas et al. | |
| 6,083,540 A | 7/2000 | Christensen et al. | |
| 6,136,334 A | 10/2000 | Viegas et al. | |
| 6,313,103 B1 * | 11/2001 | Ni et al. | 514/54 |
| 6,432,440 B1 | 8/2002 | Watts et al. | |
| 6,436,461 B1 | 8/2002 | Bouwmeesters et al. | |

FOREIGN PATENT DOCUMENTS

| | | |
|---|---|---|
| RU | 324263 | 12/1971 |
| WO | 97/25980 | * 7/1997 |
| WO | WO 98/47535 | 10/1998 |

OTHER PUBLICATIONS

Sriamornsak et al. "Calcium pectinate gel beads for controlled release drug delivery: I. Preparation and in vitro release studies", Int. J. Pharm., vol. 160(2): 207-212, 1998.*

Sriamornsak et al. "Calcium pectinate gel coated pellets as an alternative to calcium pectinate beads", Int. J. Pharm., vol. 156(2): 189-194, 1997.*

Munjeri et al. "Hydrogel beads based on amidated pectins for colon-specific drug delivery: the role of chitosan in modifying drug release", J. Controlled Release, vol. 46(3): 273-278, 1997.*

Aydin et al. "Preparation and evaluation of pectin beads", Int. J. Pharm., vol. 137(1): 133-136, 1996.*

Koji et al. "Preparation of pectin gel bead and the drug release profiles", Kobunshi Gakkai Yokoshu, vol. 47(12): 3510-3511, 1998.*

Yamada, H. "Contribution of pectins on health care", Progress in Biotech. (Pectins and Pectinases), ed. by Visser et al., publ. by Elsevier Science, pp. 173-190, 1996.*

Aspinall, G. "Pectins, Plant Gums and Other Plant Polysaccharides", The Carbohydrates (vol. IIB), eds. Pigman and Horton, publ. by Academic Press, pp. 515-521, 1970.*

Polysaccharides in Medicinal Applications, ed. by Severian Dumitriu, publ. by Marcel Dekker, pp. 211-216, 1996.*

Sriamomsak et al. "Calcium pectinate gel beads for controlled release drug delivery:I. Preparation and in vitro release studies." Int. J. Pharm., vol. 160(2), 207-212, 1998.*

Aydin et al. "Preparation and evaluation of pectin beads." Int. J. Pharm., vol. 137(1), 133-136, 1996.*

Wilfred T. Mabusela et al.: "Carbohydrate Polymers from Aloe Ferox Leaves" PHYTOCHEMISTRY, vol. 29, No. 11, 1990, pp. 3555-3558, XP002111912 Great Britain.

Gaurhari Mandal and Amalendu Das, "Structure of the dGalactan Isolated From Aloe Barbadensis Miller," Carbohydrate Research, vol. 86, 1980, pp. 247-257.

R.G. Ovodova, V.F. Lapchik and Yu S. Ovodov, "Polysaccharides of Aloe Arborescens," Plenum Publishing Corporation, 1976, pp. 1-2.

Gaurhari Mandal, Rina Ghosh and Amalendu Das. "Characterisation of Polysaccharides of Aloe Barbadensis Miller: Part III—Structure of an Acidic Oligosaccharide." Indian Journal of Chemistry, vol. 228, Sep. 1983, pp. 890-893.

A.G.J. Voragen, W. Pilnik, Jean-Francois Thibault, M.A.V. Axelos, and Catherine M.G.C. Renard, "Pectins" in "Food Polysaccharides and Their Applications." A.M. Stephen., Ed., Chapter 10, pp. 287-339, Marcel Dekker (1995).

Alan D. Cardin and H.J.R. Weintraub, "Moleculat Modeling of Protein-Glycosaminoglycan Interactions," 1987 American Heart Associattion Meeting, pp. 21-32.

Joseph Schlessinger, Irit Lax and Mark Lemmon, "Regulation of Growth Factor Activation by Proteoglycans: What is the Tole of the Low Affinity Receptors?," Cell, vol. 83, Nov. 3, 1995, pp. 357-360.

H. Edward Conrad, "Heparin-Binding Proteins-Chapter 1. Heparin vs. Heparan Sulfate," Academic Press, 1998, pp. 1-5.

H. Edward Conrad, "Heparin-Binding Proteins-Chapter 6. Heparinoid/Protein Interactions ," Academic Press, 1998, pp. 183-202.

H. Edward Conrad, "Heparin-Binding Proteins-Chapter 9. fibroblast growth factors," Academic Press, 1998, pp. 301-349.

James N. BeMiller, "An Introduction to Pectins: Structure and Properties," 189th Meeting of the American Chemical Society, Apr. 28-May 3, 1985, pp. 1-12.

Farhad Radjabi, Claudine Amar and Erna Vilkas, "Structural Studies of the Glucomannan From Aloe Vahombe," Carbohydrate Research, 1983, pp. 166-170.

T.P. Kravtchenko, I. Arnould, A.G.J. Voragen & W. Pilnik, "Improvement of the Selective Depolymerization of Pectic Substances by Chemical β-Elimination in Aqueous Solution." Carbohydrate Polymers 19, 1992, pp. 237-242.

Catherine M.G.C. Renard and Jean-Francois Thibault, "Structure and Properties of Apple and Sugar-Beet Pectins Extracted by Chelating Agents," Carbohydrate Research 244, 1993, pp. 99-114.

Colin D. May, "Industrial Pectins: Sources, Production and Applications," Carbohydrate Polymers 12, 1990, pp. 79-99.

R.R. Selvendran, B.J.H. Stevens, M.A. O'Neill, Developments in the Isolation and Analysis of Cell Walls From Edible Plants, Biochemistry of Plant Cell Walls, pp. 39-79.

Alistair M. Stephen, "Food Polysaccharides and Their Applications," Marcel Dekker, Inc., 1995, pp. 601-608.

Albersheim et al., "Splitting of Pectin Chain Molecules in Neutral Solutions," *Biochemistry and Biophysics,* 90:46-51 (1960).

Ashford et al., "An Evaluation of Pectin as a Carrier for Drug Targeting to the Colon," *Journal of Controlled Release,* 26:213-220 (1993).

Ashford et al., "Studies of Pectin Formulations for Colonic Drug Delivery," *Journal of Controlled Release,* 30:225-232 (1994).

Axelos et al., "Influence of the Substitutents of the Carboxyl Groups and of the Rhamnose Content of the Solution Properties and Flexibility of Pectins," *Int. J. Biol. Macromol.,* 13:77-82 (1991).

Cohen et al., "A Novel In Situ-Forming Ophthalmic Drug Delivery System from Alginates Undergoing Gelation in the Eye," *Journal of Controlled Release,* 44:201-208 (1997).

Fisher et al., "Assessment of Accidental Intakes of Uranyl Acetylacetonate (UAA)," *Radiation Protection Dosimetry,* 53(1-4):263-267 (1994.

Gemeiner et al., "Calcium Pectate Gel could be a Better Alternative to Calcium Alginate Gel in Multiple Applications of Immobilized Cells," *Progress in Biotechnology,* 2:76-83 (1996).
Gurny et al., "Ocular Theraphy with Nanoparticulate sYstems for Controlled Drug Delivery," *Journal of Controlled Release,* 2:353-361 (1985).
Jarvis et al., "Structure and Properties of Pectin Gels in Plant Cell Walls," *Plant, Cell and Environment,* 7:153-164 (1984).
Jeong et al., "Biodegradable Block Copolymers as Injectable Drug-Delivery Systems," *Nature,* 388:860-862 (1997).
Jeong et al., "Drug Release from Biodegradable Injectable Thermosensitive Hydrogel of PEG-PLGA-PEG Triblock Copolymers," *Journal of Controlled Release,* 63:155-163 (2000).
Langer, "Drug Delivery and Targeting," *Nature,* 392(Supp.): 5-10 (1998).
Lin et al., Carbopol/Pluronic Phase Change Solutions for Ophthalmic Drug Delivery, *Journal of Controlled Release,* 69:379-388 (2000).
Lorin et al., "Quantitative Composition of Nasal Secretions in Normal Subjects," *Journal of Laboratory and Clinical Medicine,* 80(2):275-281 (1972).
Mitterhauszerová et al., "Interaction of Aminopyrine, 4-Aminoantipyrine, Nicotine Amide, and P-Aminosalicylate with Pectic Acid," *Pharmacology,* L11:501-507 (1983). (English translation included).
Moe et al., "Alginates," *Food Polysaccharides and Their Applications,* 9:245-286 (1995).
Nurmukhambetova et al., "Interaction of Cephedrin with Polyelectrolytes," *News of the Nat'l Academy of Sciences of Republic of Kazakhstan, Chemical Series,* 3:58-61 (1995). (English translation included).
Putney et al., "Improving Protein Therapeutics with Sustained-Release Formulations," *Nature Biotechnology,* 16:153-157 (1998).
Renard et al., "Pectins in Mild Alkaline Conditions: β-elimination and Kinetics of Dementhylation," *Progress in Biotechnology, Pectins and Pectinases,* 14:603-608 (1996).
Rolin, "Pectin," in Industrial Gums, Academic Press, New York, Chapter 10, p. 258-293 (1993).
Rozier et al., "Gelrite®: A Novel, Ion-Activated, In-Situ Gelling Polymer for Ophthalmic Vehicles. Effect on Bioavailability of Timolol," *Int'l Journal of Pharmaceutics,* 57:163-168 (1989).
Shipunova et al., "Immobilization of Isoniazid on Pectin Compounds," *Institute of Chemical Sciences of Nat'l Academy of Sciences of Republic of Kazakhstan, Alma-ata,* 2:83-88 (1990).(English translation included).
Stjernschantz et al., "Anatomy and Physiology of the Eye, Physiological Aspects of Ocular Drug Therapy," *Biopharmaceutical Aspects of Ocular Drug Delivery,* 1:1-15 (1993).
Vadnere et al., "Thermodynamic Studies on the Gel-sol Transition of some Pluronic Polyols," *International Journal of Pharmaceutics,* 22:207-218 (1984).
Voragen et al., "Pectins," *Food Polysaccharides and Their Applications,* 10:287-339 (1995).
Wakerly et al., "Studies on Drug Release from Pectin/Ethycellulose Film-Coated Tablets: A potential Colonic Delivery System," *International Journal of Pharmaceutics,* 153:219-224 (1997).

Zheng et al., "Salt Effects on the Corr-linking Mechanism of Cupric-Induced Sol-Gel Transition in Alginate Solutions," *Carbohydrate Polymers,* 35:215:221 (1998).
Zhubanov et al., "Immobilization of Promedol on Poly-Sugar Supports," *A.B.Bakturov Institute of Chemical Sciences of Nat'l Academy of Sciences of Republic of Kazakhstan, Alma-ata,* (5), 27-31(English translation provided).
Zhubanov et al., "Pectic Acid and Carboxy Methyl Cellulose as Polymer Hosts for Analgesic Promedol," *A.B.Bakturov Institute of Chemical Sciences of Nat'l Academy of Sciences of Republic of Kazakhstan, Alma-ata,* 6:55-58.
Zhubanov et al., "Application of Carboxy Methyl Cellulose and Pectic Acid to Prolong Clophelin Action," *A.B.Bakturov Institute of Chemical Sciences of Nat'l Academy of Sciences of Republic of Kazakhstan, Alma-ata,* 1:61-65 (1993).
Ashford et al., "Studies on Pectin Formulations for Colonic Drug Delivery," *Journal of Controlled Release,* 30:225-232 (1994).
Aydin et al., "Preparation and Evaluation of Pectin Beads," *Int'l Journal of Pharmaceutics,* 137:133-136 (1996).
Garnier et al., "Selectivity and Cooperativity in the Binding of Calcium Ions by Pectins," *Carbohydrate Research,* 256: 71-81 (1994).
Garnier et al., "Phase Diagrams of Pectin—Calcium Systems: Influence of pH, Ionic Strength, and Temperature on the Gelation of Pectins with Different Degrees of Methylation," *Carbohydrate Research,* 240:219-232 (1993).
Mandal et al., "Structure of the $_D$-Galactan Isolated From Aloe barbadensis Miller*," *Carbohydrate Research,* 86: 247-257 (1980).
Mandal et al., "Characterisation of Polysaccharides of Aloe Barbadensis Miller: Part III—Structure of an Acidic Oligosaccharide," *Indian Journal of Chemistry,* 22(b):890-893 (1983).
Munjeri et al., "Hydrogel Beads Based on Amidated Pectins for Colon-Specific Drug Delivery: The Role of Chitosan in Modifying Drug Release," *Journal of Controlled Release,* 46:273-278 (1997).
Pilnik, W., et al., "Gelling Agents (Pectins) From Plants For The Food Industry," *Advances in Plant Cell Biochemistry and Biotechnology,* vol. 1, pp. 219-270, JAI Press Ltd., 1992.
Sriamornsak et al., "Calcium Pectinate Gel Beads for Controlled Release Drug Delivery: I. Preparation and In Vitro Release Studies," *Int'l Journal of Pharmaceutics,* 160:207-212 (1998).
Sriamornsak, "Preliminary Investigation of Some Polysaccharides as a Carrier for Cell Entrapment," *European Journal of Pharmaceutics and Biopharmceutics,* 46:233-236 (1998).
Thakur et al., "Chemistry and Uses of Pectin—A Review," *Critical Reviews in Food Science and Nutrition,* 37(1):47-73 (1997).
Tibbits et al., "Calcium Binding and Swelling Behaviour of a High Methoxyl Pectin Gel," *Carbohydrate Research,* 310:101-107 (1998).
Wakerly et al., "Studies on Amidated Pectins as Potential Carriers in Colonic Drug Delivery," *J. Pharm. Pharmacol.,* 49:622-625 (1997).

* cited by examiner

PHARMACOLOGICAL COMPOSITIONS COMPRISING PECTINS HAVING HIGH MOLECULAR WEIGHTS AND LOW DEGREES OF METHOXYLATION

This application is a continuation of application Ser. No. 09/078,204, filed May 13, 1998, now issued as U.S. Pat. No. 5,929,051, the above-listed application Ser. No. 09/078,204 is commonly assigned with the present invention and is incorporated herein by reference.

This invention relates to pectins. More specifically, this invention relates to Aloe pectins, process of isolation and their use.

Following abbreviations are used:

Ab, antibody; AG, arabinogalactan; APase, alkaline phosphatase; CDTA, trans-1,2-diaminocyclohexane-N,N', N'-tetraacetic acid; Da, dalton; DAc, degree of acetylation; DM, degree of methylation; EDTA, ethylenediaminetetraacetic acid; Gal, galactose; Gal A, galacturonic acid; GalNAc, N-acetylated galactosamine; Glc, glucose; Glc A, glucuronic acid; HM, high methoxyl; HMW, high molecular weight; HPSEC, high performance size exclusion chromatography; HR, hairy region; HT, heating; kDa, kiloDalton; LM, low methoxyl; LMW, low molecular weight; Man, mannose; MWCO, molecular weight cut-off; PBS, phosphate buffered saline (10 mM sodium phosphate, 150 mM NaCl, pH 7.4); RG, rhamnogalacturonan; RT, room temperature; SEC, size exclusion chromatography; SF, supercritical fluid; SR, smooth region; TMS, trimethylsilyl; TN buffer, 25 mM Tris, 150 mM NaCl, pH 7.4.

Pectin is a plant cell wall component. The cell wall is divided into three layers, middle lamella, primary, and secondary cell wall. The middle lamella is the richest in pectin. Pectins are produced and deposited during cell wall growth. Pectins are particularly abundant in soft plant tissues under conditions of fast growth and high moisture content. In cell walls, pectins are present in the form of a calcium complex. The involvement of calcium cross-linking is substantiated by the fact that chelating agents facilitate the release of pectin from cell walls.

Pectin is a complex polysaccharide associated with plant cell walls. It consists of an $\alpha 1$–4 linked polygalacturonic acid backbone intervened by rhamnose residues and modified with neutral sugar side chains and non-sugar components such as acetyl, methyl, and ferulic acid groups. Based on the current understanding, the general structure of pectins or pectic substances is shown in FIG. 1. The overall structure is shown on top, while the detailed 110 structure is shown on the bottom. The neutral sugar side chains which include arabinan and arabinogalactans (Types I and II) are attached to the rhamnose residues in the backbone at the O-3 or O-4 position. The rhamnose residues tend to cluster together on the backbone. So with the side chains attached this region is referred as the hairy region and the rest of the backbone is hence named the smooth region. Rhamnose residues are 1–2 linked to Gal A residues in the backbone and the configuration of this linkage has now been determined to be $\alpha$.

Pectins are traditionally used as food additives. However, their use has extended into pharmaceutical areas as well. Pectins have long been used as an anti-diarrhea agent and can improve intestinal functions. The anti-diarrhea effect is thought to be in part due to pectin's anti-microbial activity.

Pectins are also effective against gastrointestinal ulcers and enterocolitis. Pectins also influence cell proliferation in the intestines. They also have a blood cholesterol-lowering effect and exhibit inhibition of atherosclerosis. This effect is the result of interactions between pectins and bile salts. Pectins have also been shown to affect the fibrin network in hypercholesterolaemic individuals.

The ability to interact with many divalent metal ions renders pectins a strong detoxifying agent. It has been shown that pectins are effective in removing lead and mercury from the digestive tract and respiratory organs. Lately, pectins have been found to be effective for the treatment of heartburn caused by esophagus acid reflux.

Recently, so-called modified citrus pectins, which are small molecules (~10 kDa) obtained by alkaline degradation, have been found to be effective 110 in the prevention of cancer cell metastasis in laboratory animals.

Because of the presence of neutral sugar side chains and some other non-sugar components, the structure of pectins is very complex; essentially no two molecules have identical structures, which is the reason why pectin is often described using the term "pectic substances". Pectic substances is commonly used to encompass pectin, pectic acid and its salts (pectates), and certain neutral polysaccharides (arabinan, arabinogalactan, and galactan). Pectic acids or pectates are deesterified pectins.

Rhamnose, galactose, arabinose, and xylose are the most common neutral sugar components of pectins. The less common ones are glucose, mannose, and fucose. Some of the xylose residues are individually attached to Gal A residues at O-3 position. Three types of neutral sugar side chains have been identified in pectins. Arabinan consists of $\alpha 1$–5 linked arabinose. Arabinogalactan I consists of $\beta 1$-4 linked galactose with short arabinan chains attached at O-3. In arabinogalactan II, galactose is $\beta 1$-3&6 linked with arabinose attached.

Methylation occurs at carboxyl groups of Gal A residues. The degree of methyl-esterification is defined as the percentage of carboxyl groups (Gal A residues) esterified with methanol. A pectin with a degree of methylation ("DM") above 50% is considered a high methoxyl ("HM") pectin and one with a DM<50% is referred to as low methoxyl ("LM") pectin. Most of the natural pectins are HM with a few exceptions such as sunflower pectin. The degree of acetylation (DAc) is defined as the percentage of Gal A residues esterified with one acetyl group. It is assumed that only the hydroxyl groups are acetylated. Since each Gal A residue has more than one hydroxyl group, the DAc can be above 100%. DAc is generally low in native pectins except for some such as sugar beet pectin.

Pectin may contain some non-sugar components. Ferulic acid esters have been found in sugar beet pectin. They are linked to the arabinose and galactose residues in the neutral sugar side chains.

Pectins are soluble in water and insoluble in most organic solvents. Pectins with a very low level of methyl-esterification and pectic acids are only soluble as the potassium or sodium salts. As for other polymers, there is no saturation limit for pectins, but it is difficult to obtain a true solution with concentrations higher than 3–4%. Commercial pectins have a size range of $7$–$14 \times 10^4$ Da. Citrus pectins are larger than apple pectins. Viscosities of pectin solutions are generally low and so pectins are seldom used as thickening agents. The viscosity is directly related to the size, pH, and also to the presence of counterions. Addition of monovalent cations reduces viscosity.

Pectins can interact with several divalent metal ions. The order of selectivity is Cu~Pb>>Zn>Cd~Ni$\geq$Ca. This activity is the basis for pectin's detoxification effect.

The Gal A residues in the pectin backbone are α1-4 linked. Both hydroxyl groups of D-Gal A at carbon atoms 1 and 4 are in the axial position. The resulting linkage is therefore trans 1-4. This type of linkage results in increased chain stiffness of the polymer. So pectin with a flexibility parameter B between 0.072–0.017 are rigid molecules. It has been suggested that the insertion of rhamnose residues in the backbone cause a T-shaped kink in the backbone chain. An increase in rhamnose content leads to more flexible molecules. Pectins can be considered as a zigzag polymer with long and rigid smooth regions and flexible hairy regions (rich in rhamnose) serving as rotating joints. The DM also has certain effects on chain flexibility. In solution, pectin molecules have been shown to assume a right-handed helical structure.

Pectins are most stable at pH 3-4. Below pH 3, methoxyl and acetyl groups and neutral sugar side chains are removed. At elevated temperatures, these reactions are accelerated and cleavage of glycosidic bonds in the galacturonan backbone occurs. Under neutral and alkaline conditions, methyl ester groups are saponified and the polygalacturonan backbone breaks through β-elimation-cleavage of glycosidic bonds at the non-reducing ends of methoxylated galacturonic acid residues. These reactions also proceed faster with increasing temperature. Pectic acids and LM pectins are resistant to neutral and alkaline conditions since there are no or only limited numbers of methyl ester groups.

There are many enzymes that can specifically modify and degrade pectin molecules. These enzymes include endo- and exo-polygalacturonase (EC3.2.1.15 and EC 3.2.1.67), pectate lyase (EC 4.2.2.10), pectin methylesterase (EC 3.1.1.11), pectin acetylesterase, and rhamnogalacturonase. Endo-polygalacturonase is specific for non-esterified α1–4 linked Gal A residues and requires four adjacent non-esterified Gal A residues to function. This enzyme can be produced by plants, fungi, and bacteria.

Both HM and LM pectins can form gels, but by totally different mechanisms. HM pectins form gels in the presence of high concentrations of co-solutes (sucrose) at low pH. LM pectins form gels in the presence of calcium. In addition, the sugar beet pectin can form gels through cross-linking of the ferulated groups.

The calcium-LM pectin gel network is built by formation of the "egg-box" junction zones in which Ca++ ions cause the cross-linking of two stretches of polygalacturonic acids. In apple and citrus pectins, stretches of polygalacturonic acids without rhamnose insertion have been estimated to be as long as 72–100 residues. The zone is terminated by the rhamnose residue in the backbone. The calcium-LM pectin gel is thermoreversible. The calcium can therefore be added at the boiling point and gel formation occurs upon cooling. It is possible to obtain a firm resilient gel with 0.5% pectin and 30–60 mg/g Ca++. A high content of pectin with little calcium gives an elastic gel whereas a high calcium concentration with a minimum of pectin results in a brittle gel.

Addition of monovalent counterions enhances the calcium-LM pectin gel formation, i.e., less calcium is required for gel formation.

Commercial pectins are mainly extracted from apple pomace or orange peels under hot acid conditions followed by alcohol precipitation. The raw materials are first blanched, then washed to inactivate endogenous enzymes capable of degrading pectins, and to remove pigments. A common method for enzyme inactivation is alcohol treatment, i.e., cell wall fibers are prepared as the so-called alcohol insoluble residues ("AIR") or solids ("AIS").

Various extraction conditions have been used for isolation of pectins from plant cell walls. These include use of chelating agents such as EDTA, CDTA, sodium hexametaphosphate and ammonium oxalate at pH 3–6.5, hot dilute acid (HCl, pH 1.5–3), and cold dilute base (NaOH and $Na_2CO_3$; pH 10). The extraction is often performed at elevated temperatures (60–100° C.) to increase the yield. Commercial citrus and apple pectins are extracted with hot dilute acid. Since pectins are readily degraded at a pH of <3, the extraction process usually lasts briefly depending on the temperature used.

The pH of 3–6.5 at which the chelating agents are used is below the pH needed for their optimal chelating effect, but is used to minimize the pectin degradation through β-elimination. Like hot dilute acid extraction, the alkaline extraction can cause extensive degradation. It is only performed at 0–4° C. in order to minimize the degradation through β-elimination. The cold alkaline extraction is often used as the last step of a sequential extraction to remove those pectins tightly bound to cell walls.

Enzymes have also been examined for pectin extraction. They include arabinase, galactanase, polygalacturonase, and rhamnogalacturonase. The polygalacturonase-producing yeast cells have also been used directly for pectin extraction.

Characteristics of pectins extracted under different conditions may vary. Pectins extracted at elevated temperatures are smaller than those obtained at room temperature and richer in neutral sugars. The smaller size is the result of degradation under the harsher conditions. However, the yield is much higher at elevated temperature. Those pectins obtained with a chelating agent usually have a higher Gal A content. The pectins obtained under the cold alkaline conditions generally have a reduced Gal A content and a higher neutral sugar content.

Industrial pectins, either HM or LM, are mainly obtained from apple and citrus by acid extraction and alcohol precipitation. LM pectins are obtained from HM ones by chemical de-esterification. Pectins have a favorable regulatory status as a food additive. They are classified as Generally Recognized As Safe ("GRAS") in the United States and Acceptable Daily Intake ("ADI") in Europe. That is, its use is only limited by current Good Manufacturing Practice ("cGMP") requirements to meet certain specifications. These specifications include a minimal Gal A content of 65% (w/w).

HM pectin can be converted into a different type of LM pectin, i.e., amidated pectin. This is achieved by treating HM pectin with ammonia under alkaline condition in alcoholic suspensions. The methyl ester groups are replaced with amide groups. The amidated pectin has a better gel formation ability in the presence of calcium as compared to the regular LM pectin.

Many other plant sources have also been examined for pectin production. Two of them, sugar beet pulp and sunflower head, have been studied extensively. Both are abundant as raw materials. However, sugar beet pectin has a poor gel forming ability largely due to its high acetyl group content and small molecular size ($\sim 5 \times 10^4$ Da). The sunflower pectins are naturally LM and can be efficiently extracted with chelating agents. They often suffer from poor quality of raw materials and poor color quality (usually tan) of the pectin end products.

Pectins from different plant sources have different characteristics. In general, all commercial pectins including those that have gone through further processing have a certain degree of coloration as a final product. The color ranges from light yellow/brown (citrus pectin) to dark tan (apple and sunflower head pectins). The coloration is caused by the combination of two factors: natural color (pigmentation) of the raw materials and their content of polyphenols. Chemically, sunflower head pectin has a very high Gal A content and is a natural LM pectin, whereas sugar beet pectin has a relatively low Gal A content and a very high content of acetyl and ferulic acid groups. The structures of apple and citrus pectins are very similar to each other.

A set of techniques has been established for pectin analysis. The Gal A content is determined by the method using m-hydroxyldiphenyl for color formation. This assay is simpler than previous assays and has minimal interference from neutral sugars. Other assays for Gal A determination have also been described. Sugar compositions are analyzed by GLC or GC-MS using alditol acetate or trimethylsilylether ("TMS") derivatization. GLC procedures are most often used to determine methyl ester content, which involves saponification with base (0.5N) and measurement of methanol by GLC on a Poropak Q columan at 120° C. or a Carbowax 1500 column at 125° C. A capillary electrophoresis method has also been examined for determining DE of pectins. A rapid and sensitive colorimetric assay is used to measure the acetyl groups.

The size determination is achieved by various means which include viscosity, HPSEC, and gel permeation chromatography. Recently, light scattering has been proposed as a more accurate method. The intrinsic viscosities of pectins are often determined using the Ubbelohde viscometer. This is done in the presence of 0.1–0.15 M NaCl due to the electrolytic nature of pectin molecules.

The purification of pectins is mostly achieved by ion exchange chromatography and cupric precipitation. For ion exchange chromatography, DEAE sepharose CL-6B matrix and acetate buffer (pH 4.8) are most widely used. The neutral sugar content of pectins is determined following purification with these methods.

SUMMARY

Broadly, one aspect of the present invention pertains to an Aloe pectin having at least one of the following properties: degree of methylation of less than about 50% by mole; rhamnose content of from about 2 to about 15% by mole; 3-O-methyl rhamnose content of from about 0.1 to about 5% by mole; and capable of forming a gel in the presence of a solution of a calcium salt; the Aloe pectin are isolated from the leaf of an Aloe by extraction, wherein the extraction is accomplished by a supercritical fluid, a water-soluble organic solvent, an acid, an alkali, a chelating agent, a bacteria, an enzyme, or a combination thereof.

According to the present invention, pectins from gel and rind cell wall fibers of Aloe vera are extracted, isolated and identified. Serial treatment of Aloe fibers with a chelating agent such as EDTA at a pH of from about 7 to about 8.5 is most efficient method of extraction. Purified Aloe pectins are obtained by further treating Aloe pectin with an ion exchange resin. Aloe pectins contain galacturonic acid, an unusually high level of rhamnose, and 3-OMe-rhamnose. Two classes of Aloe pectin distinguished by size are obtained: the room temperature extraction generated a high-molecular-weight (HMW) pectin whereas extraction with heating produced a low-molecular-weight (LMW) pectin. Aloe pectins naturally have a low methoxyl (LM) content. Both the HMW and LMW pectins are capable of gel formation in the presence of calcium. In addition, Aloe pectins, especially the HMW pectin, forms monovalent cation-based gels at low temperatures which revert back to solution when brought to room temperature. The HMW Aloe pectin-calcium gel is a highly efficient encapsulating agent suitable for controlled release of pharmacological substances, such as proteins, antibodies, and vaccines. Aloe pectins form a matrix for antigen and antibody precipitation reactions. Further Aloe pectins form a storage matrix for pharmacological substances. Aloe pectins from pulp exhibit an off-white powder color and produced clear solutions when dissolved in water.

DETAILED DESCRIPTION

Figure 1:
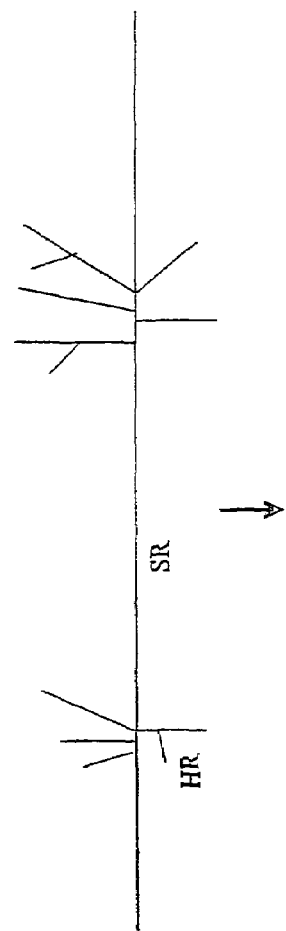
FIG. 1 shows a general structure of pectins or pectic substances, in which "HR" stands for hairy region, "SR" stands for smooth region, "AG" stands for arabinogalactan, and "RG" stands for rhamnogalacturonan.
Figure 1:
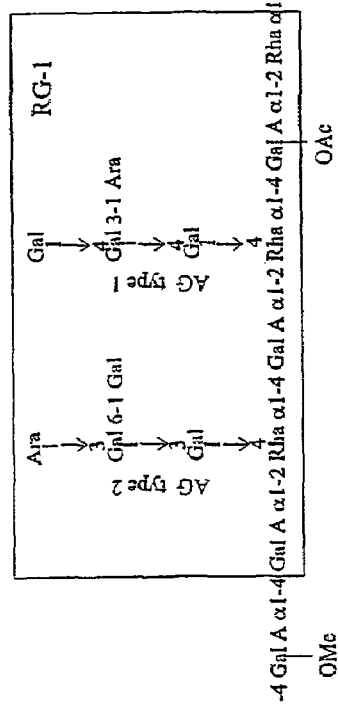
Figure 1:
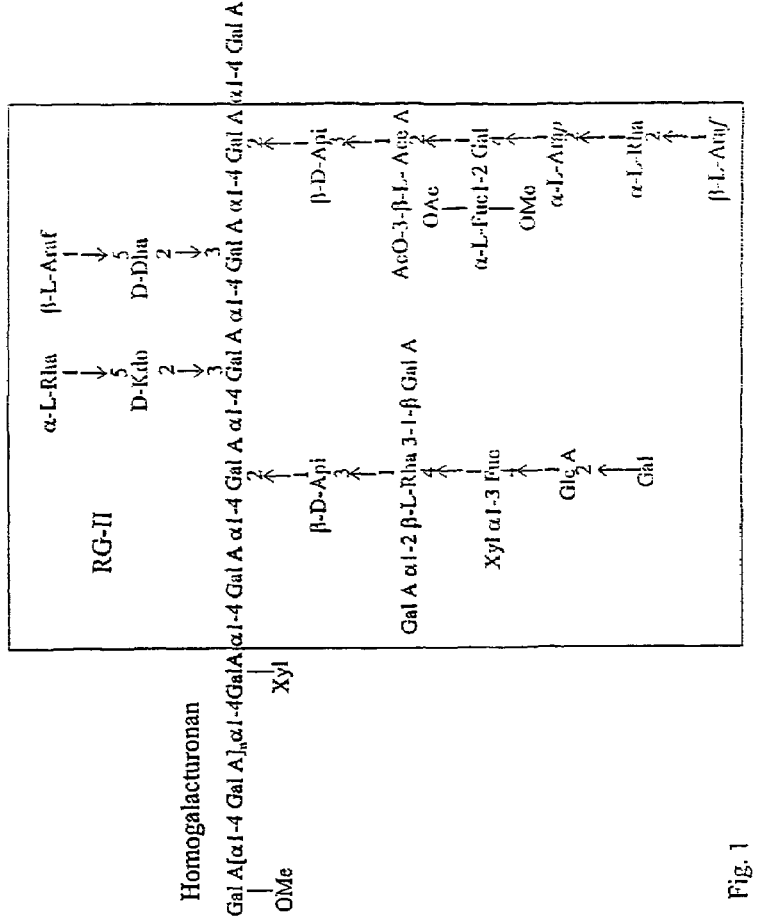

Aloe vera has long been used as a medicinal plant. It is a succulent plant adapted to live in desert and semi-desert conditions. The succulents are characterized by their possession of abundant water storage tissues. The Aloe vera leaves consist of two parts, green rind and clear pulp (i.e., inner gel or inner fillet). The latter is the water storage tissue and is most widely used for medicinal purposes. Because of its clear and slimy appearance, the pulp is often referred as the mucilaginous gel which has largely been treated as a single homogenous entity.

Pectins or pectic substances from Aloe vera and their extraction have not previously been described in any detailed manner. A pectic substance rich in Gal A has been described as the major pulp polysaccharide component. This polysaccharide with a Gal A content of 85% was isolated following hot water extraction of the alcohol precipitates of clear pulp. Neutral sugar composition analysis detected galactose, rhamnose, arabinose and trace amounts of mannose, glucose, and xylose. This finding was interpreted as a result of plant variation within the Aloe vera species and specific local conditions, as compared to the fact that most other studies identified mannose-rich polysaccharides as the major polysaccharide component in the Aloe vera pulp. A Gal A-rich polysaccharide has been obtained through hot water and ammonium oxalate extractions from whole leaf materials previously treated with boiling methanol. The Gal A content was estimated to be 55% based on paper and gas-liquid chromatography. This polysaccharide was degraded by pectinase and hence identified as pectin which in turn was claimed to be the major polysaccharide of Aloe vera. In all the above studies, no linkage studies on neutral sugars were performed, nor any detailed characterization of other chemical and physical properties (e.g., size, DM, DAc, and gel formation) of the isolated polysaccharides.

One aspect of this invention started from the clear pulp or filleted inner gel of the Aloe vera leaf. The isolation of different parts of Aloe leaf has been described in U.S. Pat. Nos. 4,735,935, 4,851,224, 4,917,890, 4,959,214, and 4,966,892, the entire content of each of these patents is hereby incorporated by reference. The clear gel contains large mesophyll (water storage) cells with very limited numbers of degenerative cellular organelles and the green rind contains much smaller cells which are rich in cellular organelles such as mitochondria and chloroplasts. It was found that following homogenization, the pulp could be separated into two major portions, soluble and insoluble. The soluble portion was shown to be rich in the β 1–4 linked mannose. The insoluble portion mainly consisted of clear cell walls or cell wall fibers (based on its microscopic appearance under low magnification following homogenization). The cell wall component in Aloe vera pulp extracts has not been previously described. The cell wall fibers contained a high level of Gal A (34% w/w), whereas the soluble portion contained <5% (w/w) of Gal A. This data clearly suggested that these cell wall fibers were potentially rich in pectin. Ensuing experiments showed that a large amount of pectin (as high as 50%, w/w) with an average Gal A content >70% (w/w) could be extracted from these pulp cell wall fibers. A large amount of pectin that is equally rich in Gal A could also be extracted from the cell wall fibers isolated from the rind. These pectins from pulp or rind fibers were named Aloe pectins.

The cell wall fibers were isolated by centrifugation or filtration following homogenization of the pulp or rind and used directly for pectin extraction without any treatment except for washing in water. The Aloe pectin could be extracted from these fibers using previously described methods, i.e., hot acid at a pH of ~1.5, cold alkali (NaOH or $Na_2CO_3$) at a pH of ~10, and chelating agents (EDTA, sodium hexametaphosphate) at a pH of 4.0–6.5. However, the most efficient extraction method that gave the highest yield was found to be the use of a chelating agent at a pH above 7 (7–8.5). The chelating agent used was EDTA. The uniqueness of this extraction procedure was the higher pH (7–8.5) used, since in all previous studies, the chelating agent has always been used at a pH<6.5 in order to minimize the degradation through β-elimination. The reason behind using this higher pH is that Aloe pectins are naturally LM (see below), a form of pectin resistant to β-elimination under alkaline conditions, and EDTA functions most efficiently at a pH above 7.

A two-step sequential extraction procedure maximized the use of fibers and yielded two types of pectin distinguished by size, HMW and LMW. The fibers were extracted first at RT followed by another extraction under HT (up to 80° C.). The RT extraction produced the HMW pectin with an average MW of $1.1 \times 10^6$ Da and the HT extraction produced the LMW pectin with an average MW of $1.9 \times 10^5$ Da. The MW was directly correlated to the intrinsic viscosities; the HMW pectin exhibited an intrinsic viscosity $\geq 550$ ml/g and as high as 978 ml/g. The MW and intrinsic viscosity of HMW Aloe pectin was much higher than those of the commercial pectins.

Aloe pectin exhibited some distinct features in sugar compositions. They contained a high level of rhamnose; the rhamnose content in Aloe pectins was at least 2 times higher than in other pectins, mainly citrus, apple, sugar beet, and sunflower. The rhamnose is a key sugar in the pectin backbone whose content affects the flexibility of the molecule. Aloe pectins also possessed a rare sugar, 3-OMe-rhamnose, which has not been described in any other pectins. Aloe pectins were found to be naturally LM, having a DM generally <30% and often <10%. They were capable of gel formation in the presence of calcium. Uniquely, Aloe pectins, especially the HMW ones, could form a monovalent cation (NaCl)-based reversible gel at low temperature (4° C.) at a very low pectin concentration (1 mg/ml). Such cold gelation has not been described for any other pectins.

The green rinds from Aloe vera leaves are generally removed as waste during production of pulp-based products. These rinds with small amounts of pulp remaining attached to them account for ~60% (w/w, wet) of the whole leaf. It was found that cell wall fibers prepared from these rinds produced an Aloe pectin yield similar to those from pulp. The Aloe pectins from rind were equally rich in Gal A and shared the same properties with the those from pulp, i.e., being naturally LM, high in MW and intrinsic viscosity (for HMW ones), and capable of calcium gel formation as well as the monovalent cation-based gel formation at low temperature (4° C.).

The Aloe pectins from the pulp fibers are off white powders as the end products and produced clear solutions as compared to the yellow to tan powders and cloudy solutions of current commercial and experimental pectins from citrus, apple, sugar beet, and sunflower. Those from the rind fibers were light green-brownish powders and produced solutions that were cloudy, but to a lesser extent than the best citrus pectins. The powder color and solution clarity of Aloe pectins from rind fibers could be substantially improved by additional alcohol rinsing.

Together, Aloe pectins are unique pectins and could be distinguished from other pectins, i.e., citrus, apple, sugar beet, and sunflower, by one or more of the following characteristics:

1) A high molecular weight ($>1 \times 10^6$ Da) and a high intrinsic viscosity (>550 ml/g).
2) A high rhamnose content.
3) Possessing 3-OMe-rhamnose.
4) Being naturally LM.
5) Capable of calcium gel formation.
6) Capable of monovalent cation-based gel formation at low temperature (4° C.).
7) Off white powders and clear solutions (Aloe pectin from pulp).

MATERIALS AND METHODS

Materials

Aloe vera (Aloe Barberdensis Miller) plants (10″) were obtained from H&P sales, Inc (Vista, Calif.) through Lowe's store. Bulk acetylated mannan (BAM) is an Aloe vera pulp extract of Carrington Laboratories, Inc. Various commercial pectins and polygalacturonic acid were used. They include HM citrus (P-9561 with a DM of 92% and P-9436 with a DM of 64%), LM citrus (P-9311 with a DM of 28%), polygalacturonic acid (P-1879) from Sigma Chemical Co., HM citrus (PE100 with a DM of 67%) from Spectrum Chemical Co., and HM citrus (CU401) and apple (AU201) from Herbstreith-Fox KG. Following reagents were also obtained from Sigma Chemical Co.; disodium EDTA, tetrasodium EDTA, endo-polygalacturonase, alkaline phosphatase, alkaline phosphatase-antibody (IgG) conjugate, Folin-Ciocalteu's reagent, imidazole, and all neutral and acidic sugars used. The alkaline phosphatase substrate pNPP was obtained from Pierce. Sodium hexametaphosphate was obtained from Fluka Chemie AG.

Generally, BAM may be prepared from Aloe leaves as follows:
1. Aloe leaves are washed, sliced open and filleted to remove the leaf rind. The clean (substantially anthraquinones free) inner gel is retained while the green rind is discarded.
2. The filleted material is homogenized (creparo) and extensively filtered with a Finisher Model 75 (FMC, Chicago, Ill.) to remove most of the pulp.
3. The clear viscous gel is acidified to a pH of approximately 3.2 with dilute HCl.
4. The acidified gel is then extracted with four volumes of 95% ethanol at ambient temperature. Floating material is removed, then the alcohol/water mixture is siphoned off while the solid precipitate is collected by centrifugation. Most alcohol/water soluble substances such as organic acids, oligosaccharides, monosaccharides, anthraquinones and inorganic salts are eliminated by the alcohol extraction process.
5. The solid Aloe vera extract is then washed with fresh alcohol, centrifuged, freeze dried, and ground to a white powder.

The product is stable at room temperature in the freeze-dried form for several years if protected from additional moisture. The detailed procedures for producing substantially anthraquinone-free Aloe gel, for producing substantially anthraquinone-free Aloe juice, for extracting active chemical substance(s) from an Aloe leaf, for preparing BAM and for extracting from an Aloe leaf substantially non-degradable lyophilized ordered linear polymers of mannose have been described in Carrington's U.S. Pat. Nos. 4,735,935, 4,851,224, 4,917,890, 4,957,907, 4,959,214, and 4,966,892, the entire content of each of which is incorporated by reference. The uses of Aloe products have been described in Carrington's U.S. Pat. Nos. 5,106,616, 5,118,673, 5,308,838, 5,409,703, 5,441,943, and 5,443,830, the entire content of each of which is hereby incorporated by reference.

EXAMPLE 1

Light and Electron Microscopy of Leaf Sections

Fresh Aloe vera leaves were sectioned with a surgical blade into 2–3 mm-thick pieces. The sections were directly observed under the light microscope (Olympus BH-2). For histological analysis, fresh Aloe vera leaves were fixed in 10% formalin in PBS and sections were stained with toluidine blue.

Figure 2:
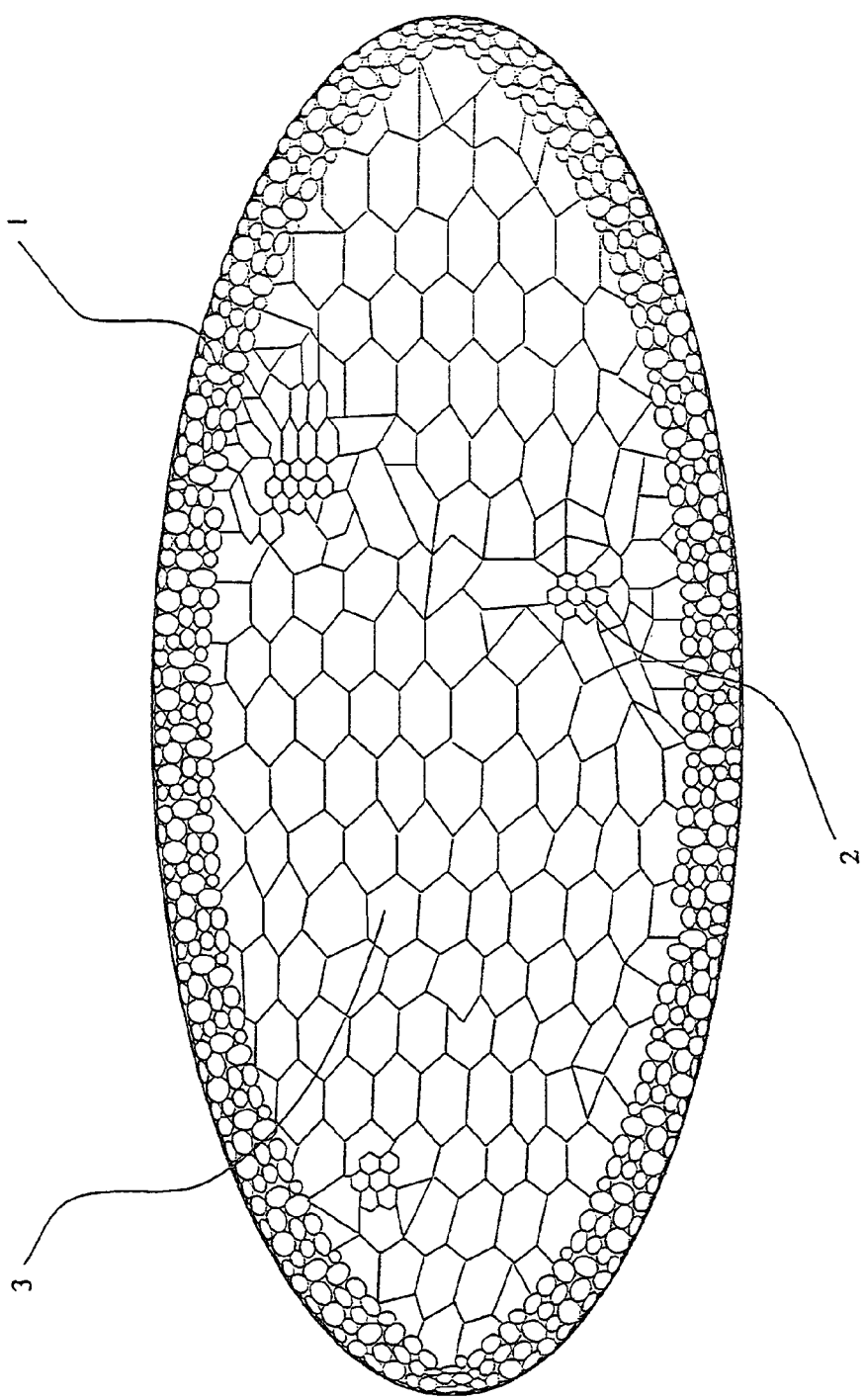
FIG. 2 is a cross-section schematic representation of Aloe Vera leaf structure.
Figure 3:
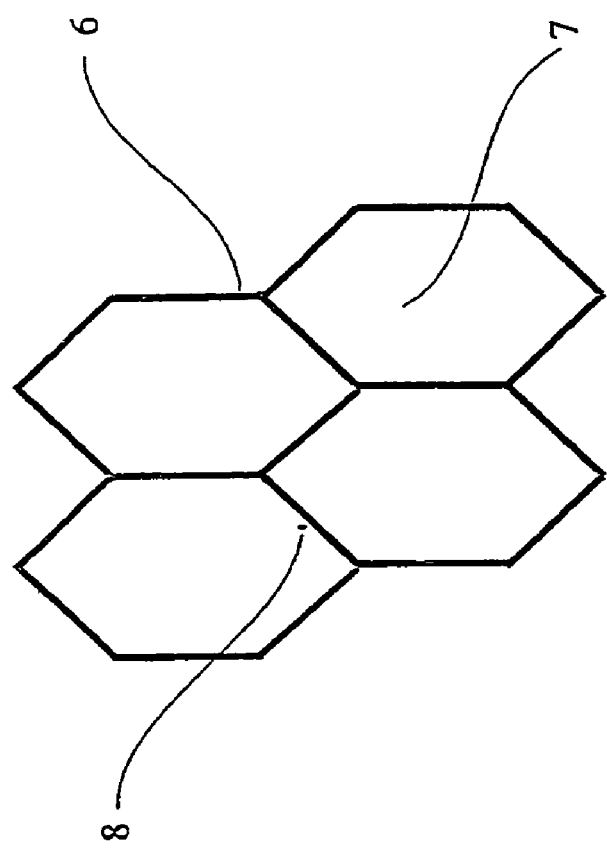
FIG. 3 shows the structural components of Aloe Vera pulp mesophyl cells.

The protocols for tissue fixing and staining for electron microscopy followed that described by Trachtenberg (Annuals of Botany, 1984, 53, pp. 227–236). Briefly, fresh pulp tissue blocks were fixed at room temperature in 4% glutaraldehyde in 0.2 M cacodylate-HCl buffer (pH 7.2) for 2 hrs followed by fixing for 2 hrs in 2% osmium tetroxide in the same buffer. The tissues were dehydrated and sectioned after embedding in resin. The tissue sections were stained with uranyl acetate, and examined using a Zeiss 10C electron microscope. The light microscopy of leaf sections showed that the pulp (3) consisted of large clear mesophyll cells, which exhibited a hexagonal shape (FIG. 2). The sizes of these cells were very large, often more than 300 µm in width. The walls of these cells were clear and transparent. The cells in the rind (1) were much smaller as compared to those in the pulp (3) (FIG. 2). Electron microscope examinations revealed, in addition to cell walls (6), liquid gel (7), only the cell membranes in the pulp along with very limited number of degenerative cellular organelles (8) (FIG. 3). Nuclei, chloroplasts and other cellular organelles such as mitochondria were only observed in the green rind and vascular bundles, (2) (FIG. 2).

EXAMPLE 2

Light Microscopy of Cell Wall Fibers

BAM was dissolved in water at 2 mg/ml. The solutions were stirred at room temperature for 3 hrs or at 4° C. for overnight. They were then centrifuged at low speed (1000 rpm or 180 g) for 15 min (Beckman TJ-6). The pellet was collected, washed once with water, and dried (Centrivap, Labconco). The weight of pellet was determined following drying. A small sample of the pellet was examined under the light microscope (Olympus BH-2). The insoluble pellet materials from the pulp extracts appeared to be fibers at low magnification (4×), and to be clear transparent sheets at higher magnification (10× and 40×) with an appearance identical to those clear pulp cell walls described above. With less extensive homogenization, some of these fibers still retained the original structural features of the mesophyll cells. These observations together indicate that the insoluble fibers are derived from the pulp mesophyll cell walls.

EXAMPLE 3

Extraction of Aloe Pectins

Preparation of cell wall fibers Two types of cell wall fibers were used, alcohol-treated and non-alcohol-treated. The alcohol-treated fibers were isolated from BAM by centrifugation. BAM was dissolved in water at 2 mg/ml. The solution was then centrifuged at 180 g for 10 min. The pellet, consisting of cell wall fibers, was harvested and washed three times with water before being dried. Since BAM has gone through alcohol precipitation, these fibers are therefore similar to those alcohol insoluble residues or solids (AIS) that are commonly prepared for extraction of pectins from other plant tissues.

The non-alcohol-treated fibers include the crude pulp and rind fibers.

Crude pulp fibers were those retained by the coarse filtration during production of BAM and other pulp-based products. They are the same as those found in BAM, except for being larger in size and not alcohol-treated. They were collected with a no. 18 sieve (1 mm opening) with minimal loss and washed three times with water. The green rind, accounting for ~60% wet weight of the whole leaf, are generally discarded as waste by manufacturers. It contained the green rind proper as well as some pulp left behind after filleting. The fibers were isolated from them in a similar way to those from pulp following homogenization. They were washed extensively, at least three times, with water, then dried, and stored at RT before being used for pectin extraction.

Figure 4:
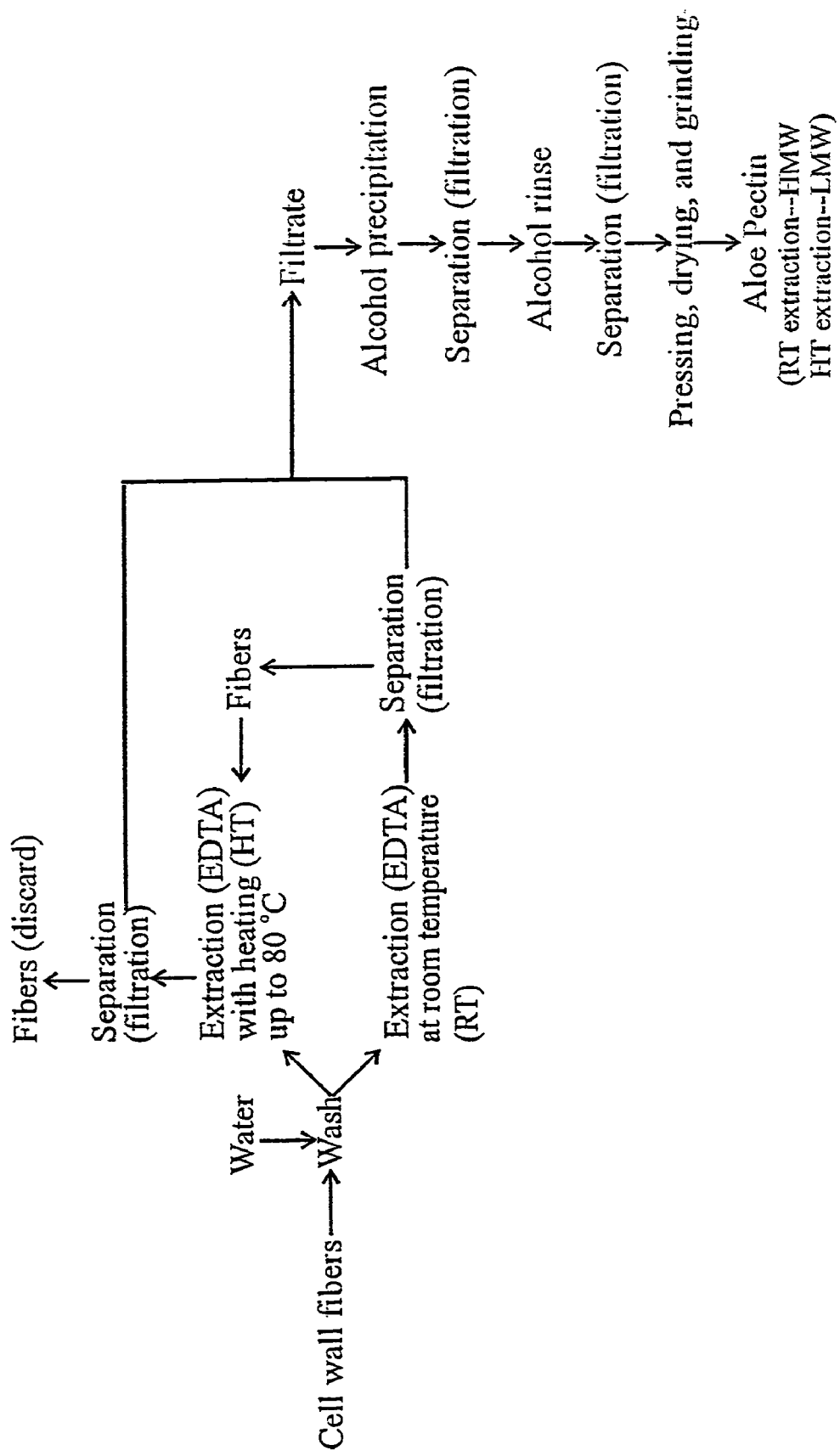
FIG. 4 is a flow chart for sequential Aloe pectin extraction (at room and high temperatures) using EDTA as the chelating agent.

Extraction The chelating agent EDTA was used for extraction of Aloe pectins from the cell wall fibers. The fibers were suspended in water at 0.2–2% (w/v). The EDTA stock solution was prepared at 0.5 M and a pH of 7.0 or 8.0 and added to the fiber suspension. The final concentration of EDTA used was 25 mM. The final pH of the fiber suspensions was adjusted with NaOH to the indicated values. The extraction was done with stirring at either RT or with HT, or in a sequential manner—RT extraction followed by HT extraction. HT was carried out up to 80° C. and then stopped before the separation step. In the sequential extraction, the remaining fibers following the RT extraction were re-suspended to the same volume in water without washing and fresh EDTA was added at the same concentration as for the RT extraction (FIG. 4). Following extraction, remaining fibers were removed by centrifugation (500 g, 15 min) or by filtering with a no. 18 sieve followed by gauze sponge filtering. The gauze sponges (4×4, 8 ply) were used with three pieces together and set up in a disc filter frame. The sponges were washed with water before use. The gauze sponge filtration was highly efficient in removing the residual small fibers after the sieve filtration. When necessary, the extract was passed through the sponge filter twice. The filtrate was essentially clear. For quantitative studies on yields from sequential extraction, fibers were always removed by centrifugation following the first round of extraction at RT. Alcohol (ethanol) was added to the clear supernatant or filtrate to a final concentration of 75% (v/v). The precipitates were collected by centrifugation (500 g, 15 min) or with the no. 18 sieve and washed twice with 75% alcohol. The alcohol wash step was necessary to remove residual EDTA. The precipitates were then pressed to remove alcohol, dried, and stored at RT before use.

The extraction of Aloe pectins with the chelating agent EDTA was found to be highly efficient and a yield as high as 50% (w/w) could be obtained. The pectins obtained had an average galacturonic acid content above 70% (w/w) (Table 1). The pH was found to have a major effect on the pectin yield with EDTA extraction (Table 2). A 5 mg/ml fiber suspension in water had a pH of 3.7 (3–4). The pH of the fiber suspension was 7.7 (7.5–8.0) following addition of pH 8.0 EDTA stock to a final concentration of 25 mM. A pH of 6.4 (6.3–6.5) was obtained when a pH 7.0 EDTA stock solution was used to give a final concentration of 25 mM. The pH 5.0 was obtained by using a pH 5.0 sodium acetate buffer at a final concentration of 20 mM, a common condition for pectin extraction. It was found that there was no major difference in yield following RT extraction at a pH from 5.0 to 7.7 (Table 2). A major effect of pH, however, was found during HT extraction. A yield increase by >20% was noted at pH 7.7 as compared to pH 5.0 or pH 6.4 during HT extraction of fresh fibers (Table 2). Furthermore, a nearly 2-fold increase in yield was noted when the remaining fibers from the first round of RT extraction were extracted under HT with fresh pH 8.0 EDTA added as compared to using pH 7.0 EDTA (Table 2). The pH values of the fiber suspensions did not change significantly at the end of RT extraction (Table 3). However, after re-suspending in water and addition of fresh EDTA, the pH (~8.5) of the suspensions was actually higher than that of EDTA stock solutions (pH 8.0) (Table 3). It was further found using the fresh fibers under HT extraction that the pH 8.5 extraction did give a much higher yield, more than 2-fold higher than that at pH 5.0 and ~40% higher than that at pH 7.7 (Table 4). Increasing the pH to 9.0, however, did not improve the yield much further (<10%) as compared to pH 8.5. Ensuing experiments also showed that a substantial increase (20%) in yield was also obtained with RT extraction at pH 8.5 (Table 4).

RT was less efficient than HT during extraction. The yield was similar between these two conditions provided the RT extraction was extended in time. The yield by RT extraction approached the maximum by ~4 hrs. Further extension of the extraction time did not significantly improve the yield. The yield of the second extraction with HT varied depending on the length of the first RT extraction; therefore the yield with HT would be higher if RT extraction was performed for only 1 hr, or lower when the RT extraction was performed for 4 hrs or longer (Table 2).

Repeated extraction under the same conditions produced a progressively lower yield. The yield decreased by approximately half with each extraction. The remaining fibers can therefore be suspended in half the volume from the previous extraction.

EDTA and fiber concentrations also influenced the extraction efficiency. When 25 mM EDTA was used with a 2 mg/ml fiber suspension, a yield between 50–60% could be obtained with a single extraction under HT. When using a 5 mg/ml fiber suspension with the same EDTA concentration, the yield decreased to 30%. With the sequential RT to HT extraction as shown in FIG. 4, a combined yield of 40–50% could be readily obtained. No difference in yield was noted between alcohol treated and non-alcohol-treated fibers.

Other chelating agents were also considered for Aloe pectin extraction. Ammonium oxalate was not used because it is considered a toxic agent. Using sodium hexametaphosphate, a considerable yield was obtained; however, this agent was difficult to remove because of precipitate formation in alcohol solution and an acid (HCl or $HNO_3$) precipitation step was required before the alcohol wash.

Other conditions were also examined for Aloe pectin extraction. Hot dilute acid and cold alkaline solutions are two other common conditions for pectin extraction. Both of them can cause extensive degradation. Commercial pectins from citrus and apple were extracted under the hot dilute acid condition. Using this condition for the Aloe pectin, the pH of fiber suspensions was adjusted to 1.5 with HCl followed by HT up to 80° C. The yield obtained is much lower compared to using EDTA extraction (Table 5). The extraction by HT in water alone yielded virtually no alcohol precipitable materials. Renault and Thibault (Renault and Thibault, Carbohydrate Research, 1993, 244, pp. 99–114) reported that extraction of apple and sugar beet fibers in PBS (pH 6.5) with HT (80° C.) generated a high yield similar to that by EDTA extraction. Using this condition, only a low yield was obtained from the Aloe vera pulp fibers (Table 5). Cold alkaline extraction was performed with 50 mM NaOH or 50 M $Na_2CO_3$ at 4° C. The pH in suspension was 11.5 with 50 mM NaOH and 10.5 with 50 mM $Na_2CO_3$. After 1 hr at 4° C., a very low yield was obtained with 50 mM $Na_2CO_3$. No alcohol precipitable materials were obtained with 50 mM NaOH. When the extraction was done at RT for 1 hr, no yield was obtained with either agent, suggesting that pectins are rapidly degraded under these conditions.

Together, these results showed that extraction with EDTA at pH 7.0–8.5 is the most efficient extraction method for Aloe pectin. With the sequential RT to HT extraction scheme outlined in FIG. 4, a high yield (40–50%, w/w) could be obtained along with production of both HMW and LMW Aloe pectins. The uniqueness of this extraction procedure was the higher pH (7.0–8.5) used. The reason behind this higher pH is that Aloe pectins are naturally LM (see below) which are more resistant to β-elimination under alkaline conditions and EDTA functions most efficiently at a pH above 7.0. In addition, EDTA is more soluble at a pH above 7.0 and can therefore be more readily removed during alcohol precipitation and wash steps.

The green rind fibers produced a similar yield of pectin compared to the pulp fibers when extracted with the pH 8.0 EDTA (Table 6). This rind pectin was equally rich in Gal A (Table 1). The amount of fibers obtained from the rind was more than 10 times higher than that from the pulp (per unit of leaves) (Table 6). This is consistent with the fact that the rinds consisted much smaller cells as compared to the pulp (FIGS. 2 and 3). Together, these results indicated that a very large amount of Aloe pectin can be obtained from the rind portion of the leaf, which is currently discarded as waste materials by some manufacturers.

To extract LM/HMW Aloe pectins with EDTA at about room temperature, the workable pH range appeared to be between about 5 and about 8.5, preferably about 8–8.5. To extract LM/LMW Aloe pectin with EDTA at elevated temperature (for example at about 80° C.), the workable pH ranges appeared to be between about 5 and about 8.5, preferably about 8.0. At pH of higher than 6.5, EDTA extraction of HM pectins from other sources at elevated temperature would lead to the degradation of the products. For the extraction of pectins from other plant sources using EDTA or other chelating agents, the reported pH ranges are 4–6.5.

EXAMPLE 4

Pectin Purification by Ion Exchange Chromatography

The ion exchange chromatography was performed on a Pharmacia Biotech AKTA explorer chromatography system. The column was three Pharmacia Hi-trap Q, 5 ml cartridges connected in series. Aloe pectins were dissolved in water at 1 mg/ml and loaded onto the column at a flow rate of 1 ml/min. After washing with 15 ml of water, bound materials were eluted with a linear gradient of NaCl (0–1.0 M). The column eluant was monitored by UV absorbance at 215, 254, and 280 nm. Fractions containing pectin formed precipitates which were collected by low speed centrifugation, pooled, and redissolved in water. They were then desalted by passing through a Sephadex G-25 column. The pectin-containing fractions were collected, dried, and stored at room temperature.

TABLE 1

Galacturonic acid content of Aloe pectins.

| Origin of cell wall fibers* | EDTA extraction conditions† | UA content (%, w/w) | DM# (%, mole/mole) | Phenol (%, w/w) |
|---|---|---|---|---|
| Pulp, BAM 20926 (AP B1) | slight alkaline, HT | 64 | — | — |
| Pulp, BAM 20926 (AP B8) | Acidic, HT | 89 | — | — |
| Pulp, BAM 20926 (AP B8-2) | slight alkaline, HT | 85 | — | — |
| Pulp, BAM 10679 (AP B9) | Acidic, HT | 84 | — | — |
| Pulp, BAM 10679 (AP B9-2) | slight alkaline, HT | 86 | — | — |
| Pulp, BAM 10679 (AP B10) | acidic, HT | 69 | — | — |
| Pulp, BAM 10679 (AP B14) | acidic, HT | 87 | — | — |
| Pulp, BAM 10679 (AP B15) | slight alkaline, RT | 81 | 35 | 0.064 |
| Pulp, BAM 10679 (AP B15-2) | slight alkaline, HT | 79 | 40 | 0.036 |
| Pulp, BAM 10679 (AP 10679) | slight alkaline, HT | 77 | 9.4 | 0.05 |
| Pulp, crude (AP B16) | slight alkaline, RT | 93 | 1.1 | <0.03 |
| Pulp, crude (AP B16-2) | slight alkaline, HT | 92 | 17.5 | <0.03 |

TABLE 1-continued

Galacturonic acid content of Aloe pectins.

| Origin of cell wall fibers* | EDTA extraction conditions† | UA content (%, w/w) | DM# (%, mole/mole) | Phenol (%, w/w) |
|---|---|---|---|---|
| Pulp, crude (AP 97-1) | slight alkaline (RT & HT) | 91 | 4.4 | <0.03 |
| Rind, crude (AP rind B1) | slight alkaline, RT | 81 | 4 | 0.045 |
| Rind, crude (AP rind B1-2) | slight alkaline, HT | 84 | 9.5 | 0.041 |
| Rind, crude (AP rind B2) | slight alkaline, RT | 75 | — | 0.219 |

*The numbers following BAM (bulk acetylated mannan) are BAM lot numbers. Aloe pectin serial numbers are indicated in parentheses and -2 designates pectins obtained by HT extraction following the RT extraction.
†Slight alkaline, pH 7.0–8.5; acidic, pH 5.0; RT, room temperature; HT, heating.
DM, degree of methylation.

TABLE 2

Aloe pectin yield (%, w/w) obtained under various extraction conditions.

| | Extraction temperature† | Extraction Conditions* | | |
|---|---|---|---|---|
| | | pH 7.0 EDTA and 20 mM pH 5.0 NaAc (pH 5.0) | pH 7.0 EDTA (pH 6.4) | pH 8.0 EDTA (pH 7.7) |
| Exp 1 | HT | 22 | 26 | 32.3 |
| Exp 2 | RT (1 hr) | — | 14.4 | 16 |
| | HT | — | 15 | 24.4 |
| | Total yield | — | 29.4 | 40.4 |
| Exp 3 | RT (4 hr) | 28 | 31.6 | 30 |
| | | (DM = 30%)# | (DM = 29%) | (DM = 19%) |
| | HT | 5.6 | 5.8 | 13.5 |
| | Total yield | 33.6 | 37.4 | 43.5 |

*The 5 mg/ml crude pulp fiber suspensions were used. Numbers in brackets indicates the pH of the fiber suspensions after addition of EDTA.
†RT, room temperature; HT, heating.
DM, degree of methylation.

TABLE 3

The pH of fiber suspensions before and after extraction with EDTA.

| | Extraction Conditions* | | |
|---|---|---|---|
| | pH 7.0 EDTA and 20 mM pH 5.0 NaAc | pH 7.0 EDTA | pH 8.0 EDTA |
| pH after addition of EDTA | 5.0 | 6.4 | 7.7 |
| pH following RT extraction | 5.06 | 6.4 | 7.74 |
| pH after re-suspending and addition of fresh EDTA and before HT extraction | 5.15 | 6.8 | 8.56 |

*The 5 mg/ml crude pulp fiber suspensions were used which had a pH of 3.5. RT, room temperature; HT, heating.

TABLE 4

Further evaluation of the effect of pH on the
Aloe pectin yield (%, w/w) with EDTA extraction.

| | | Extraction with heating in the presence of EDTA* | | |
|---|---|---|---|---|
| Fiber source | Extraction temperature† | pH 5.0 (pH 7.0 EDTA in 20 mM pH 5.0 NaAc) | pH 7.7 (pH 8.0 EDTA alone) | pH 8.5 (pH 8.0 EDTA and pH adjustment with NaOH) |
| Pulp, crude | HT | 18 (DM = 27%)# | 32.4 (DM = 29%) | 44.8 (DM = 30%) |
| Rind, crude | RT | 26 (DM = <10%) | 26 (DM = <10%) | 32 (DM = <10%) |

*The 5 mg/ml fiber suspensions were used. DM, degree of methylation.
†RT, room temperature; HT, heating.
DM, degree of methylation.

TABLE 5

Aloe pectin yields obtained with non-EDTA-based extraction.

| | Extraction conditions* | | | |
|---|---|---|---|---|
| | Heating in water | Heating at pH 1.5 (adjusted with HCl) | Heating at pH 6.5 (pH 6.5 PBS) | 50 mM Na$_2$CO$_3$ (pH 10.5) at 4° C. for 1 hr | 50 mM Na$_2$CO$_3$ (pH 10.5) at RT for 1 hr |
| Yield (%, w/w) | 0 | 9.6 | 10.6 | 7.5 | 0 |

*The 5 mg/ml crude pulp fiber suspensions were used.

TABLE 6

Extraction of Aloe pectin from green rind fibers.

| | Fresh Aloe Vera leaves | |
|---|---|---|
| | Pulp | Rind |
| Wet weight after separation | 188 g (33%) | 376 g (67%) |
| Fibers obtained after homogenization, 18# sieve filtration, and washing | 0.34 g | 5.23 g |
| Pectin yield* | | |
| EDTA-RT (1$^{st}$ round) | 10.8% (w/w) | 17.5% (w/w) |
| EDTA-HT (2$^{nd}$ round) | 26.4% (w/w) | 25.5% (w/w) |
| Total | 37.2% (w/w) | 43% (w/w) |
| Pectin powder color | White-off white | Light green-brown |

*The fibers were extracted at 5 mg/ml and RT extraction was performed for 1 hr.

EXAMPLE 5

Uronic Acid Assay

The m-hydroxyldiphenyl-based uronic acid assay was carried out as described by (Blumenkratz and Asboe-Hansen (1973), Analytical Biochemistry 54, pp. 484–489). Briefly, samples or standards in 200 µl pyrogen-free water were mixed with 1.2 ml concentrated H$_2$SO$_4$ containing 0.0125 M sodium tetraborate and then immediately put on ice. The samples were then kept in boiling water for 5 min followed by cooling in a water-ice bath. 20 µl of 0.15% (w/v) m-hydroxyldiphenyl in 0.5% NaOH was then added to each reaction. After mixing, the samples were kept at room temperature for 30 min. The absorbance at 520 nm was then determined. Gal A was used to generate a standard curve (0, 1, 2, 4, 6, 8, and 10 µg). Mannose was used as a neutral sugar control. All samples were tested at 20 µg or less.

The average Gal A content of different Aloe pectins was above 70% (Table 1). There were no significant differences between the Gal A contents of pectins extracted under different conditions.

EXAMPLE 6

Sugar Composition and Linkage Analysis

Fluorophore-Assisted Carbohydrate Electrophoresis ("FACE") is a fast and simple technique for sugar composition analysis. It allowed for initial examination and comparison of various samples and was carried out according to the procedure provided with the FACE sugar composition analysis kit (Glyco, Inc.). Briefly, polysaccharides were hydrolyzed with 2N trifluoroacetic acid (TFA) at 100° C. for 5 hrs and then labeled with a fluorescent dye (AMAC, 2-aminoacridone) and electrophoresed. Carbohydrate bands were visualized under a UV light (Fotodyne 3–3000). Besides the neutral sugar standards provided in the kit, Gal A and Glc A were also used.

Composition analysis by TMS derivatization Samples were subjected to preliminary aqueous hydrolysis in 2N TFA for 6 hrs at 105° C. TFA was removed by evaporation under nitrogen and the partially hydrolyzed carbohydrate residue was subjected to methanolysis in 2M methanolic HCl for 16 hrs at 80° C. to complete the hydrolysis with the formation of methyl glycosides. Methanolic HCl was removed under nitrogen and the methyl glycosides were subjected to N-acetylation in methanol-pyridine-acetic anhydride for 6 hrs at room temperature. The solvents were evaporated and the residues were trimethylsilylated using Tri-Sil at 80° C. for 20 min. The resulting TMS-methylglycosides, were analyzed by GC-MS using a 30 m. DB-5 capillary column equipped with a mass selective detector.

Linkage analysis The Hakomori method (Hakomori, Journal of Biochemistry, 1984, 55, pp. 205–212) of methylation with superdeuteride reduction was used. The samples were suspended in DMSO and subjected to sonication at 60° C. for 36 hrs in a bath type ultrasonicator. Samples were then methylated using potassium methylsulfonyl carbanion (3.6 M) followed by the addition of a 50–100 fold excess of methyl iodide. The partially methylated material was isolated by reverse phase cartridge chromatography and subjected to carboxyl reduction. The samples were then purified and subjected to remethylation according to the Hakomori procedure. The sample was then hydrolyzed and converted to partially methylated alditol acetates. The resulting PMAA derivatives were analyzed by GC-MS using a 30 m SP-2300 capillary column.

Sugar composition analysis using FACE showed that the extracted pectin was richer in Gal A as compared to the cell wall fibers. The detailed compositions were obtained with TMS derivatization and GC-MS analysis. In Table 7, the sugar compositions of three samples, AP 10679, AP 10679 (purified as described in Example 4), and AP97-1, are presented (See also Table 1). Sample AP 10679 was obtained by HT extraction from alcohol-treated fibers as described in Example 3. Sample AP97-1 was a trial production sample extracted from non-alcohol-treated crude fibers. The fibers were extracted twice at room temperature followed by HT extraction. The pectins obtained from the two extraction conditions were combined and the ratio of the pectins extracted at RT over those by HT extraction was ~2:1.

TABLE 7

Sugar composition (%, mole/mole) of Aloe pectins

| | AP 10679 (5)* | AP 10679 (purified) (5) | AP 97-1 (5) |
|---|---|---|---|
| Ara | 4.2 | 1.8 | 4.0 |
| Rha | 11.1 | 4.4 | 10.3 |
| 3-Me-Rha | 0.8 | 0.5 | 0.8 |
| Fuc | 0.6 | 0.4 | 0.6 |
| Xyl | 3.9 | 1.2 | 2.4 |
| Man | 1.6 | 0.3 | 3.5 |
| Gal | 8.5 | 6.8 | 14.8 |
| Glc | 1.1 | 0.7 | 0.4 |
| Gal A | 67.5 | 83 | 63.2 |
| DM | LM (9.4) (natural) | LM (natural) | LM (4.4) (natural) |
| DAc | 9.0 | ≦2.8 | 9.1 |
| Total phenol (%, w/w) | 0.058 | — | <0.03 |
| Rha/Gal A | 0.16 | 0.05 | 0.16 |
| Gal/Gal A | 0.13 | 0.08 | 0.23 |

*The number in parentheses is the reference number. See the reference list at the end of Table 15.

The sugar composition analysis showed that Gal A was the primary sugar, 67% in AP 10679 and 63.2% in AP 97-1. The rhamnose and galactose are the most abundant neutral sugars, accounting for 10–11.1% and 8.5–14.8%, respectively. Among the minor neutral sugars, a modified sugar, 3-OMe-rhamnose was detected, which accounted for about 10% of total rhamnose. The sugar compositions were very similar between the two samples, except for a small amount (<0.5%) of GalNAc and glycerol detected in AP 10679.

The purified AP 10679 showed an enriched Gal A content and a reduced neutral sugar content, suggesting that some of the neutral sugars detected in the unpurified sample may not be associated with the pectin. The rhamnose and galactose were still the most abundant neutral sugars. The 3-OMe-rhamnose was also still present, again accounting for ~10% of total rhamnose.

The sugar linkage data on AP 10679 and AP 97-1 are shown in Tables 8 and 9. The major linkages detected were 1, 4 linked Gal A and 1, 2 linked rhamnose. The 1, 4 linkage for Gal A is the same as for other pectins. No other linkage was detected for Gal A (Tables 8 and 9). Besides the 1, 2 linkage, rhamnose residues were also 1, 2, 4 linked with a small portion (0.6 or 0.7%) 1, 2, 3 linked. The rhamnose with the 1, 2 and 1, 2, 4 linkages accounted for the major portion of the total rhamnose residues, suggesting that most of the rhamnose residues detected are in the pectin backbone. Since the 1, 2, 4 linked rhamnose was much more than the 1, 2, 3 linked in both samples, the neutral sugar side chains are therefore most likely linked to the backbone at the O-4 position of rhamnose residues.

TABLE 8

Glycosyl linkage in AP 10679.

| Monsaccharide | Linkage | % total area* | Area ratio |
|---|---|---|---|
| Arabinose | terminal (fur) | 7.2 | 0.39 |
| | terminal (pyr) | 0.6 | 0.03 |
| | 5-linked (fur) | 1.1 | 0.06 |
| | 2-linked (pyr) | 0.7 | 0.04 |
| | 2,3-linked (pyr) | 0.6 | 0.03 |

TABLE 8-continued

Glycosyl linkage in AP 10679.

| Monsaccharide | Linkage | % total area* | Area ratio |
|---|---|---|---|
| Rhamnose | terminal | 4.0 | 0.22 |
| | 2-linked | 14.7 | 0.8 |
| | 3-linked | 2.2 | 0.12 |
| | 2,3-linked | 0.7 | 0.04 |
| | 2,4-linked | 6.3 | 0.34 |
| Xylose | terminal | 5.5 | 0.3 |
| | 4-linked | 4.8 | 0.26 |
| | 2,4-linked | 1.2 | 0.07 |
| Fucose | terminal | 3.9 | 0.21 |
| | 3,4-linked | 1 | 0.05 |
| Mannose | terminal | 1.2 | 0.07 |
| | 4-linked | 4 | 0.22 |
| Galactose | terminal | 5.7 | 0.31 |
| | 3,4-linked | 1.4 | 0.06 |
| | 3,6-linked | 0.6 | 0.03 |
| | 4,6-linked | 0.5 | 0.03 |
| Glucose | 4-linked | 2.5 | 0.14 |
| Galacturonic acid | terminal | 2.8 | 0.15 |
| | 4-linked | 18.3 | 1 |
| Glucuronic acid | terminal | 2.6 | 0.14 |
| | 2-linked | 2.3 | 0.13 |
| | 2,4-linked (Gal UA/GlcUA) | 0.9 | 0.05 |

*Percent of total area is normalized to 1-4 linked galacturonic acid.

TABLE 9

Glycosyl linkage in AP97-1.

| Monsaccharide | Linkage | % total area* | Area ratio |
|---|---|---|---|
| Arabinose | terminal (fur) | 6.2 | 0.34 |
| | terminal (pyr) | 0 | 0 |
| | 5-linked (fur) | 1.6 | 0.09 |
| | 2-linked (pyr) | 0.8 | 0.04 |
| | 2,3-linked (pyr) | 0.7 | 0.04 |
| Rhamnose | Terminal | 3.8 | 0.21 |
| | 2-linked | 11.1 | 0.61 |
| | 3-linked | 1.5 | 0.08 |
| | 2,3-linked | 0.6 | 0.03 |
| | 2,4-linked | 10.7 | 0.58 |
| Xylose | Terminal | 6.9 | 0.38 |
| | 4-linked | 2.9 | 0.16 |
| | 2,4-linked | 1.1 | 0.06 |
| Fucose | Terminal | 3.3 | 0.18 |
| | 3,4-linked | 0.8 | 0.04 |
| Mannose | Terminal | 2.7 | 0.15 |
| | 4-linked | 8.2 | 0.45 |
| Galactose | Terminal | 5.3 | 0.29 |
| | 3,4-linked | 1.5 | 0.08 |
| | 3,6-linked | 0.5 | 0.03 |
| | 4,6-linked | 0.6 | 0.03 |
| Glucose | 4-linked | 1.7 | 0.09 |
| Galacturonic acid | Terminal | 2.6 | 0.14 |
| | 4-linked | 18.3 | 1 |
| Glucuronic acid | Terminal | 2.3 | 0.12 |
| | 2-linked | 2.5 | 0.14 |
| | 2,4-linked (Gal UA/GlcUA) | 0.9 | 0.05 |

*Percent total area is normalized to 1-4 linked galacturonic acid.

TABLE 10

The sugar composition (%, mole/mole) of Aloe pectin in comparison with commercial pectins (unpurified)

| | AP 10679 (5)* | AP 97-1 (5) | Apple (1) | Apple K (9) | Apple U (9) | Lemon A (4) | Lemon B (4) | Citrus (8) | Citrus (2) | Sugar beet (6) |
|---|---|---|---|---|---|---|---|---|---|---|
| Ara | 4.2 | 4.0 | 1.4 | 7.23 | 3.42 | 2.9 | 2.7 | 1.44 | 3.3 | 13.2 |
| Rha | 11.1 | 10.3 | 2.9 | 2.03 | 1.83 | 1.8 | 1.4 | 1.74 | 1 | 3.2 |
| 3-Me-Rha | 0.8 | 0.8 | — | — | — | — | — | — | — | — |
| Fuc | 0.6 | 0.6 | — | — | — | — | — | — | — | — |
| Xyl | 3.9 | 2.4 | 2.2 | 1.24 | 0.46 | 0.17 | 0.16 | 0.16 | 0.1 | 0.3 |
| Man | 1.6 | 3.5 | tr | 0.11 | 0.11 | 0.17 | 0.16 | 0.21 | 0.2 | 0.3 |
| Gal | 8.5 | 14.8 | 3.4 | 9.6 | 7.43 | 6.0 | 6.7 | 5.41 | 4.8 | 7.1 |
| Glc | 1.1 | 0.4 | 4.7 | 18.87 | 8.57 | 0.5 | 0.87 | 0.89 | 0.6 | 0.4 |
| Gal A | 67.5 | 63.2 | 85 | 64 | 76.68 | 88 | 88 | 90.2 | 90 | 58.8 |
| DM | LM (9.4) (natural) | LM (4.4) (natural) | LM (28) | LM (42) | HM (73.6) | HM (71.5) | HM (72) | — | HM (71.4) | HM (66.6) |
| DAc | 9 | 9.1 | — | — | 1.4 | 1.6 | — | <1 | 25.4 | |
| Rha/Gal A | 0.16 | 0.16 | 0.034 | 0.004 | 0.015 | 0.02 | 0.016 | 0.016 | 0.011 | 0.054 |
| Gal/Gal A | 0.13 | 0.23 | 0.04 | 0.15 | 0.1 | 0.068 | 0.076 | 0.06 | 0.053 | 0.12 |
| Powder color | White/off white | | Tanned | | | Light yellow/brown | | | | Tanned |
| Solution clearness | Clear | | | | | Cloudy | | | | Cloudy |

*Reference number. See the reference list at the end of Table 15.

TABLE 11

The sugar composition (%, mole/mole) of purified Aloe pectin in comparison with other purified pectins.

| | AP 10679 (purified)/ Chela* (5)# | Citrus/ Acid† (15) | Citrus/ Acid (2) | Apple/ Chela (11) | Apple/ Acid (9) | Apple/ Acid (9) | Apple/ Chela (12) | Sugar beet/ Acid (13) | Sugar beet/ Chela (13) | Sugar beet/ ChSS (11) |
|---|---|---|---|---|---|---|---|---|---|---|
| Ara | 1.8 | 1.9 | 1.8 | 13 | 2.77 | 2.1 | 4 | 9.8 | 2.9 | 16 |
| Rha | 4.4 | 0.6 | 0.7 | 2 | 1.16 | 0.58 | 1 | 3.1 (+Fuc) | 1.1 (+Fuc) | 2 |
| 3-Me-Rha | 0.5 | — | — | — | — | — | — | — | — | — |
| Fuc | 0.4 | — | — | — | — | — | — | — | — | tr |
| Xyl | 1.2 | 0.2 | 0.1 | 1 | 1.04 | 0.35 | 1 | 0.3 | 0.3 | tr |
| Man | 0.3 | 0.1 | — | — | 0.11 | — | tr | 0.06 | 0.02 | — |
| Gal | 6.8 | 2.7 | 3.2 | 3 | 5.2 | 5.02 | 3 | 4 | 3.3 | 6 |
| Glc | 0.7 | 0.2 | 0.2 | 1 | 2.08 | 1.75 | 1 | 0.2 | 0.3 | tr |
| Gal A | 83 | 66.3 | 94 | 88 | 87.38 | 89.95 | 90 | 82 | 92 | 76 |
| DM | LM (natural) | HM (79.1) | HM (72) | — | HM (75.8) | HM (72.3) | — | HM (62) | HM (60) | — |
| DAc | ≦2.8 | 2 | <1 | — | — | — | — | 35 | 15 | — |
| Rha/Gal A | 0.053 | 0.009 | 0.007 | 0.022 | 0.013 | 0.006 | 0.011 | (0.038) | (0.012) | 0.026 |
| Gal/Gal A | 0.08 | 0.04 | 0.034 | 0.034 | 0.06 | 0.06 | 0.033 | 0.0 | 0.036 | 0.078 |

*Chela, extracted with chelating agent.
†Acid, extracted under the acidic condition.
Reference number. See the reference list at the end of Table 15.

TABLE 12

The sugar composition (%, mole/mole) of Aloe pectins in comparison with others extracted with chelating agents.

| | AP 10679 (5)* | AP 97-1 (5) | Apple (14) | Apple (12) | Apple (11) | Citrus (10) | Rape-seed (3) | Sunflower (8) | Sugar beet (12) | Sugar beet (15) | Potato (7) |
|---|---|---|---|---|---|---|---|---|---|---|---|
| Ara | 4.2 | 4.0 | 28 | 15 | 4.9 | 4 | 27 | 0.75 | 25 | 15 | 2.8 |
| Rha | 11.1 | 10.3 | 3 | 2.9 | 1.6 | 1 | 2.0 | 1.77 | 2.5 | 2.2 (+fuc) | 2.2 |
| 3-Me-Rha | 0.8 | 0.8 | — | — | — | — | — | — | — | — | — |
| Fuc | 0.6 | 0.6 | 0.01 | 0.1 | — | — | 0.6 | — | — | — | 0.3 |
| Xyl | 3.9 | 2.4 | 4 | 3.9 | 1.4 | <1 | 8.2 | 0.31 | — | 0.6 | 0.5 |
| Man | 1.6 | 3.5 | 1 | — | tr | 1 | 3.0 | 0.1 | — | 0.3 | 1.3 |
| Gal | 8.5 | 14.8 | 8 | 8.4 | 6.5 | 2 | 9.2 | 0.68 | 7.7 | 5 | 14.6 |
| Glc | 1.1 | 0.4 | 1 | 1.2 | 3.9 | 2 | 3.2 | 1.18 | — | 0.7 | 0.9 |
| Gal A | 67.5 | 63.2 | 55 | 67.4 | 81 | 90 | 47 | 95.6 | 64.1 | 76 | 77.3 |
| DM | LM (9.4) (natural) | LM (4.4) (natural) | HM (82) | HM (75) | HM (60) | HM (79) | — | LM (38.5) (natural) | HM (58) | HM (64) | ~50% |

TABLE 12-continued

The sugar composition (%, mole/mole) of Aloe pectins in comparison with others extracted with chelating agents.

| | AP 10679 (5)* | AP 97-1 (5) | Apple (14) | Apple (12) | Apple (11) | Citrus (10) | Rape-seed (3) | Sunflower (8) | Sugar beet (12) | Sugar beet (15) | Potato (7) |
|---|---|---|---|---|---|---|---|---|---|---|---|
| DAc | 9.0 | 9.1 | 13 | 12 | 2 | 2 | — | 2.01 | 33 | 20.6 | — |
| Rha/Gal A | 0.16 | 0.16 | 0.055 | 0.043 | 0.019 | 0.011 | 0.045 | 0.008 | 0.039 | 0.029 | 0.028 |
| Gal/Gal A | 0.13 | 0.23 | 0.15 | 0.12 | 0.08 | 0.02 | 0.19 | 0.01 | 0.12 | 0.066 | 0.189 |

*Reference number. See the reference list on the next page.

REFERENCES FOR TABLES 7, 10, 11 AND 12

1. Axelos, M. A. V. and Thibault, J. F. (1991). Int. J. Biol. Macromol. 13, 77–82.
2. Axelos, M. A. V. Thibault, J. F., and Lefebvre, J. (1989). Int. J. Biol. Macromol 11, 186–191.
3. Eriksson, I., Andersson, R., and Aman, P. (1997). Carbo. Res. 301, 177–185.
4. Kravtchenko, T. P. Voragen, A. G. J., and Pilnik, W. (1992). Carbo, Polymers 18, 17–23, 1992.
5. Analysis reports on Aloe pectins for Complex Carbohydrate Research Center at University of Georgia.
6. Guillon, F. and Thilbault, J-F. (1990). Carbo. Polymers 12, 353–374.
7. Jarvis, M. C., Hall, M. A., Threlfall, D. R., and Friend, J. (1981). Planta 152, 93–100.
8. Miyamoto, A. and Chang, K. C. (1992). J. Food Sci. 57, 1439–1443.
9. Pilnik, W. (1981). APRIA symposium on fiber in human nutrition. P. 91, Paris.
10. Ros, J. M. Schols, H. A. and Voragen, A. G. J. (1996). Carbo. Res. 282, 271–284.
11. Renard, C. M. G. C., Voragen, A. G. J. Thibault, J. F., and Pilnik, W. (1990), Carbo. Polymers 12, 9–25.
12. Renard, C. M. G. C, and Thibault, J-F., and Pilnik, W. (1990). Carbo. Res. 154, 177–187
13. Roumbouts and Thilbault (1986). Carbo. Res. 275, 343–360.
14. Schols et al (1995). Carbo. Polymers 8, 209–223.
15. Thilbault, J. F. (1998). Carbo. Polymers 8, 209–223.
16. Thilbault, J-F. and Dreu, R. D., Geraeds, C. C. J. M., and Rombouts, F. M. (1998). Carbo. Polymers 9, 119–131.

The linkage experiments also detected Glc A which was not detected in the composition experiments because its peaks overlapped those of the much stronger Gal A peak (Tables 8–9). Among other sugars, galactose was either 1, 3, 4 or terminally linked with a small portion 1, 3, 6 or 1, 4, 6 linked, arabinose(fur) either 1, 5 or terminally linked, arabinose (pyr) 1, 2 linked, fucose 1, 3, 4 linked, xylose 1, 4 linked, mannose mainly 1, 4 linked, glucose 1, 4 linked, and Glc A 1, 2 linked. The 1, 4 linked mannose is similar in linkage to the mannan found in liquid gel inside pulp mesophyll cells. Thus, presence of 1, 4 linked mannose could be the result of residual liquid gel still associated with the mesophyll cell wall fibers.

EXAMPLE 7

Acidic Polysaccharide Gel Electrophoresis

The gel electrophoresis for separation of acidic polysaccharides was carried out as described by Misevic (Misevic, Methods in Enzymology, 1989, 179, pp. 95–110) using the Bio-Rad minigel apparatus. Tris-boric acid (pH 9.0) was used as both the gel and running buffer. A 15% polyacrylamide gel was found to be optimal. The gels were stained with alcian blue and destained with 2% (v/v) acetic acid.

EXAMPLE 8

Enzyme Digestion of Aloe Pectin

Aloe pectin was dissolved in 50 mM sodium acetate buffer (pH 5.0). Endo-polygalacturonase (EC3.2.1.15) was added at various concentrations (0.25–25 mU). After incubation at room temperature for 1 hr, samples were immediately mixed with the sample buffer (pH 9.0) and separated by acidic polysaccharide gel electrophoresis as described above.

Endo-polygalacturonase is specific for α1–4 linked Gal A residues in pectins. The results showed that this enzyme degraded Aloe pectin in a dose-dependent manner; the higher the enzyme concentration, the smaller the size of remaining pectin molecules as demonstrated by faster migration in the gel. No effect was observed on heparin, a non-pectin control. This result confirmed the 1–4 linkage between Gal A residues in Aloe pectin and also indicated that the configuration of this linkage is a.

EXAMPLE 9

Acetylation, Methylation, and Total Phenol

Acetylation and Methylation

The acetyl groups were detected by derivatization with hydroxylamine HCl and ferric acid. Acetylcholine (0.001–0.0005 N) was used as the standard. Samples were tested at various concentrations (0.2–0.8 mg/ml). Both samples and standards were prepared in 1 ml 0.001 N acetate buffer and mixed with 2 ml of hydroxylamine HCl reagent (2 M hydroxylamine HCl mixed 1:1 with 3.5 N NaOH). After about 1 min, 1 ml 4 N HCl was added. After another 1 minute, 1 ml of 0.37 M ferric chloride (in 0.1 N HCl) was added. Following mixing, the absorbance at 540 nm was measured. The amount of acetyl groups in mole was determined by extrapolating against the linear regression curve of the standard. The degree of acetylation (DAc) of the pectins was expressed as % (mole/mole) of Gal A.

Degree of methylation (DM) was determined using the selective reduction method described by Maness (Maness, Analytical Biochemistry, 1990, 185, pp. 346–352) with modifications. Pectin samples were prepared in 1 M imidazole-HCl buffer (pH 7.0). For each test, 1 mg sample in 400 µl was used. NABH$_4$ (40 mg) was added and the sample was kept on ice for 1 hr to selectively reduce the methyl-esterified Gal A residues. Then, 0.1 ml acetic acid was added to remove the remaining NaBH$_4$. The sample was diluted with 0.5 ml water and the pectins were precipitated with 4 volumes of 95% ethanol. After being dried, the sample was dissolved in water and the Gal A content was determined as described above. The control went through the same steps except for the addition of $NaBH_4$. The DM was determined by the following formula: DM=[(moles of Gal A in the control-moles of Gal A in the reduced)/moles of Gal A in the control]×100.

It was found that the alcohol precipitation and drying steps could be eliminated without affecting the results. Thus, after addition of acetic acid, 9.5 ml of water was added, giving a pectin concentration of 0.1 mg/ml or 20 µg/200 µl—the upper limit for the uronic acid assay.

Determination of Total Phenol

The method described by Rombouts and Thibault (Carbohydrate Research, 1986, 282, pp. 271–284) was used. Pectin samples in 0.6 ml water were mixed with 0.6 ml of Folin-Ciocalteu reagent. After 3 min, 0.6 ml of 1 M sodium carbonate was added. The mixtures were left at RT for 1 hr before the 750 nm absorbance values were determined. Ferulic acid was used as a standard. Some precipitates formed after pectin samples were mixed with the reagents. They appeared to be colorless and removed by centrifugation at 3,000 rpm for 15 min before absorbance measurement at 750 nm.

Methylation, Acetylation, And Total Phenol

The results obtained with the selective reduction method showed that Aloe pectins had a DM below 40% and often <10% (Table 1). The DMs of two pectin samples (citrus LM and citrus HM) from Sigma Chemical Co. were determined by this method to be 24% (+3.5) and 58% (+3.5), being consistent with the values (28% and 64%, respectively) provided by the supplier.

It was found that Aloe pectins obtained by RT extraction had a DM lower by 5–10% as compared to those obtained by HT extraction (Table 1). It was also found that RT extraction at pH 7.7 produced pectin with a DM lower by ~10% as compared those by RT extraction at pH 5.0 or 6.4 (Table 2). This latter observation appeared to be consistent with the fact that increasing pH at RT favors the demethylation reaction over the β-elimination. No difference was noted when HT extraction was performed at various pH (5.0–8.5) (Table 4).

The rind pectin was also LM (Table 1). In fact, they consistently exhibited a DM below 10% (Tables 1 & 4). This suggests that the rind pectins may naturally have an even lower DM as compared to those of pulp pectins.

Acetylation was detected with a chemical method as described above. AP 10679 and AP 97-1 exhibited a DAc of 9.0% and 9.1%, respectively. However, the DAc of the purified AP 10679 was found to be ≦2.8%. This suggests that Aloe pectin also has a low level of acetylation (Table 7).

Aloe pectins had a very small amount of phenols (0–0.22% w/w) (Table 1).

EXAMPLE 10

Molecular Weight Determination By Size Exclusion Chromatography (SEC)

The SEC was performed using TSK-Gel G5000 PWXL column (Toso Haas). Samples were prepared at 0.3 mg/ml in water with 0.05% (w/v) sodium azide. 50 µl of the sample was injected and eluted with 0.05% sodium azide at 1 ml/min. Refractive index was measured in line. Pullulans ($4.04 \times 10^5$, $7.88 \times 10^5$, and $1.66 \times 10^5$ Da) were used as standards. The molecular weight was calculated against the linear regression line of the standards.

Aloe pectins generally exhibited only one major peak. This is consistent with findings on other pectins. Aloe pectins obtained by RT extraction had an average molecular weight of $1.1 \times 10^6$ ($0.785$–$1.36 \times 10^6$ Da), which was ~5 times larger than the average size $1.9 \times 10^5$ ($0.375$–$6.08 \times 10^5$ Da) of those obtained by HT extraction. Pectins extracted with HT from remaining fibers of RT extraction had a similar molecular size to those extracted with HT from fresh fibers.

The sizes of pectins were also analyzed by acidic polysaccharide gel electrophoresis. Profiles obtained from gel electrophoresis were consistent with the results obtained by size exclusion chromatography, i.e., the sizes of pectins obtained by RT extraction were much larger (migrated much slower in gel) than those by HT extraction. Using this technique, it was also observed that pectins extracted with HT at low pH (5.0) had a comparable size to those obtained by RT extraction. This suggests that pH is the most important factor in determining the size of pectins obtained, although heating is also important. These findings are consistent with the general properties of pectins, i.e., they are most stable at low pH (3–4) and low temperature.

Together, the pectins obtained by RT extraction or HT extraction at low pH (5.0) are grouped as high-molecular-weight (HMW) pectins and those obtained by HT extraction at pH 7.0 or above are grouped as low-molecular-weight (LMW) pectins. Thus, two classes of Aloe pectins distinguished by size can be readily obtained by changing extraction temperature. This could be best achieved by following the sequential extraction scheme outlined in FIG. 4.

The average size of HMW Aloe pectins ($1.1 \times 10^6$ Da) is much larger than that ($0.7$–$1.4 \times 10^5$ Da) of commercial pectins, which is close to that of LMW Aloe pectins. To confirm this size difference, three commercial citrus pectin samples, one LM (P-9311, lot 74H1092; Sigma Chemical Co.) and two HM (P-9436, lot 96H0788; Sigma Chemical Co. and PE100, lot JR071, Spectrum Chemical Co.), were analyzed by SEC under the same conditions. Their sizes ranged from $2.0$–$4.6 \times 10^5$ Da, being much lower than those of HMW Aloe pectins. The sizes of citrus pectins are usually larger than those of apple pectins (Pilnik and Voragen, Advances in Plant Biochemistry and Biotechnology, 1992, 99, pp. 219–270).

EXAMPLE 11

Viscosity

Intrinsic viscosities were determined using the Ubbelhode viscometer (No. 2). Pectins were dissolved in 0.1 M NaCl at a concentration of 0.005–0.2% (w/v) (Owens, Journal of the American Chemical Society, 1946, 68, pp. 1628–1632; Axelos, International Journal of Biological Macromolecules, 1989, 11 pp. 186–191.) The intrinsic viscosity, (η) was calculated using double Huggins ($\eta_{sp}/c = \eta + k' \eta^2 c$) and Kraemer ([In $\eta_{rel}]/c = \eta + k'' \eta^2 c$) extrapolation (to zero concentration) (Axelos and Thilbault, International Journal of Biological Macromolecules, 1989, 11 pp. 186–191; Doublier and Cuvelier, Carbohydrates in Food, ed. A. C. Eliasson, Marcel Dekker, New York, 1996, pp. 283–318). The averages of the numbers obtained with these two equations are presented in Table 13 in comparison with MW.

The highest intrinsic viscosity (978 ml/g), was found with a rind pectin obtained by RT extraction. The intrinsic viscosities of HMW Aloe pectins were generally higher than those of LMW ones. The intrinsic viscosities of HMW Aloe pectins were also generally higher than those of the commercial citrus and apple pectins tested here. This is also consistent with the differences in molecular weight between HMW Aloe pectins and commercial pectins.

TABLE 13

Intrinsic viscosities of Aloe pectins.

| Pectins | Fiber source | Size (Da) | Intrinsic viscosity ($\eta$, ml/g) |
|---|---|---|---|
| AP 97-1 | Pulp, crude | $1.36 \times 10^6$ (HMW) | 740 |
| AP 10679 | Pulp, BAM | $3.75 \times 10^4$ (LMW) | 68 |
| AP B15 | Pulp, BAM | $7.87 \times 10^5$ (HMW) | 262 |
| AP B15-2 | Pulp, BAM | $6.45 \times 10^4$ (LMW) | 68 |
| AP B16 | Pulp, crude | $1.06 \times 10^6$ (HMW) | 550 |
| AP B16-2 | Pulp, crude | $6.08 \times 10^5$ (LMW) | 337 |
| AP rind B1 | Rind, crude | ND* | 978 |
| AP rind B1-2 | Rind, crude | ND | 523 |
| AP rind B2 | Rind, crude | ND | 846 |
| Sigma LM citrus | — | $2.18 \times 10^5$ | 51 |
| Sigma HM citrus | — | $2.02 \times 10^5$ | 178 |
| Spectrum HM citrus | — | $4.56 \times 10^5$ | 297 |
| HF HM citrus | — | ND | 201 |
| HF HM apple | — | ND | 277 |

*Not determined.

EXAMPLE 12

Calcium Gel Formation

Aloe pectins at various concentrations in water were mixed with calcium chloride solution at various concentrations along with commercial LM and HM pectins. After standing at RT for up to 24 hrs, the tubes were inverted. If the sample flowed easily, it was considered that no gel formation occurred. If the sample did not flow or deform under its own weight, gel formation had occurred. If the sample did not flow, but deformed (i.e., the surface did not keep a straight line perpendicular to the side of the tube when tubes were held at a horizontal position), the system was considered as a soft gel. The results showed that Aloe pectin obtained by either RT or HT extraction from either pulp or rind fibers formed firm gels in the presence of calcium as did the LM citrus pectin and polygalacturonic acid (Table 14) Under the same conditions, the HM citrus pectin did not form gels. This is consistent with the fact that the Aloe pectin is a LM pectin. Pectins from citrus and apple are naturally HM pectins. LM pectins are obtained by demethylating the HM pectins. Since no harsh conditions were applied during the extraction of Aloe pectins, especially with RT extraction, the Aloe pectin is a natural LM pectin.

With a 0.2% Aloe pectin solution, the minimum concentration of calcium chloride required for gel formation was determined to be 1–2 mM (50–100 mg $CaCl_2$/g pectin). With increasing concentrations of pectin and/or calcium chloride, the gel became gradually firmer. It was noted that the HMW Aloe pectins formed gels more readily than LMW Aloe pectins in that it took less time for gels formation and the gel seemed firmer.

Increasing the ionic strength facilitated the calcium gel formation. The speed of gel formation gradually increased with increasing NaCl concentrations (0–0.2 M) after the addition of a fixed amount of calcium chloride.

EXAMPLE 13

Monovalent Cation-Based Gel Formation

Aloe pectins were dissolved in water at various concentrations. The pectin solutions were mixed at RT with equal volumes of 0.3 M NaCl (2×saline), 0.3 M NaCl and 40 mM sodium acetate (pH 5.0), or 2×PBS (pH 7.4). The final volumes were 1 or 2 ml. The tubes (12×75 mm) were then placed in a fridge at 4° C. or on ice (0° C.). The gel formation was judged as described in Example 12. The tubes were then returned to RT to determine if the gel reverted back to solution. Various NaCl concentrations (0.05–1 M) were tested for gel formation. The potassium salt (KCl) was also tested. The salt and pectin solutions were always mixed in equal volumes (1:1). For determining the effect of endo-polygalacturonase on the gel formation, pH 5.0 acetate buffer was added to pectin solutions to a final concentration of 20 mM. The enzyme was then added at indicated concentrations. After standing at RT for 30 min, the solutions were mixed with equal volumes of 0.3 M NaCl and then placed on ice. The gel formation was examined as above.

When an Aloe pectin solution in 0.15 M NaCl (physiological saline) was cooled to 4° C., a gel was obtained. The gel was firm and free standing when kept at 4° C. just as the calcium gel; it turned quickly back to solution when brought to RT (22° C.). This reversible solution-gel transition could be repeated many times by changing the temperature.

Unlike the gel formation in the presence of calcium which occurred efficiently with both HMW and LMW Aloe pectins, the monovalent cation-based gel formation only occurred efficiently with HMW Aloe pectins obtained from either pulp or rind fibers. The sample AP 97-1 and similar ones, which had molecular weights of >1×$10^6$ Da, could produce firm gels at concentrations as low as 0.1 mg/ml in the presence of 0.15 M NaCl. Such gels were also clear when the pectin concentrations were 5 mg/mil or less. With higher pectin concentrations (>5 mg/ml), gels were firmer and slightly cloudy. With a 1 ml volume, a gel could form in 15 min after the tube was placed on ice and returned to solution in about the same time after it was brought back to RT. The gel, however, did not revert back to solution at a temperature as high as 15° C. The gel could form at pH 5.0 (in saline with 20 mM pH 5.0 sodium acetate) as well as pH 7.4 (in PBS).

The LMW (0.375–6.08×$10^5$ Da) Aloe pectins only formed such gels at higher concentrations (≧5 mg/ml). At 1 mg/ml, only soft gels could be obtained with some of the LMW samples in 0.15 M NaCl. The smallest Aloe pectin sample (0.375×$10^5$ Da) formed no gel at 1 mg/ml in 0.15 M NaCl. A soft gel was only obtained with this sample at a pectin concentration of 10 mg/ml in 0.2 M NaCl. This suggests that the efficiency of the monovalent cation-based gel formation is dependent on the size of the pectin molecules. As shown in Example 8, Aloe pectin could be degraded by endo-polygalacturonase. Thus, 300 μl of 2 mg/ml AP97-1 pectin solution in 20 mM pH 5.0 sodium acetate was digested with this enzyme at various concentrations before mixing with an equal volume of 0.3 M NaCl and placed on ice. The results showed that the control (no enzyme added) formed a gel and the sample with the highest enzyme concentration remained a solution (Table 15). Between the control and the highest enzyme concentration, the transition from solution to gel was evident, i.e., the gel became softer with an increase in the enzyme concentration until a complete solution was obtained at the highest enzyme concentration. This result indicates that the size of the Aloe pectin molecules is an important factor in monovalent cation-based gel 110 formation.

The gel formation was also dependent on the NaCl concentration. In 0.1 M NaCl, only soft gels were obtained with samples like AP 97-1. The firm gels only formed in 0.15 M and 0.2 M NaCl. Whereas the gel formed at 0.15 M NaCl was fully reversible when the gel was brought back to RT, the gel formed at 0.2 M NaCl was not readily reversible, especially for the HMW Aloe pectins. After standing at RT for 1 hr or longer, syneresis often occurred with the gel formed at 0.2 M NaCl, i.e., the liquid was separated from the gel. With higher NaCl concentrations ($\sqrt[3]{}$ 0.4 M), precipitates formed at RT. The precipitates were white and amorphous at high NaCl concentrations (0.6–1 M) and appeared to be fine granules at 0.4 M NaCl.

Such cold gelation is also sensitive to the species of monovalent cations used. With KCl (0.05–1 M), no cold gel formation occurred, although precipitates were formed at higher KCl concentrations ($\geq$0.4 M) at RT.

Precipitation of pectins at high salt concentrations and RT has been previously observed. However, such a reversible monovalent cation (NaCl)-based cold gelation under the physiological condition (0.15 M NaCl, pH 7.4) has not previously been described with any other pectins. So far, no such gelling system has been identified with any other polymers or substances in literature. Using the commercial polygalacturonic acid, LM and HM pectins, no such monovalent cold gelation was obtained.

EXAMPLE 14

Use of Aloe Pectin as An Encapsulating Agent for Controlled Release

The APase and APase-antibody (APase-Ab) conjugate were used for encapsulation. They were chosen because the release activity can be directly measured using the APase substrate pNPP. Aloe pectins at 10 or 15 mg/ml in water were mixed with APase or APase-Ab at a final concentration of 10–20 µg/ml. The mixture at RT was dripped over about 30 minutes into a 200 mM $CaCl_2$ bath to make beads ~1 mm in diameter. Beads isolated by decantation were washed and kept in water at 4° C. First, spontaneous release was examined in relation to pectin concentration and the size of pectin molecules. For release experiments, the same numbers of beads (3–5) were incubated at room temperature in 100 µl of water, saline (150 mM NaCl), TN buffer, or buffers without NaCl at various pH for 2 hrs. The pH 3–5 was achieved with 10 mM sodium acetate buffer and the pH 6–8 was achieved with Tris buffer. At the end of the incubation, 10 µl of the incubation media was removed and mixed with 100 µl of the APase substrate (pNPP). After 15 min, the reaction was stopped with 50 µl 2M NaOH and the absorbance at 405 nm was measured.

Figure 5:
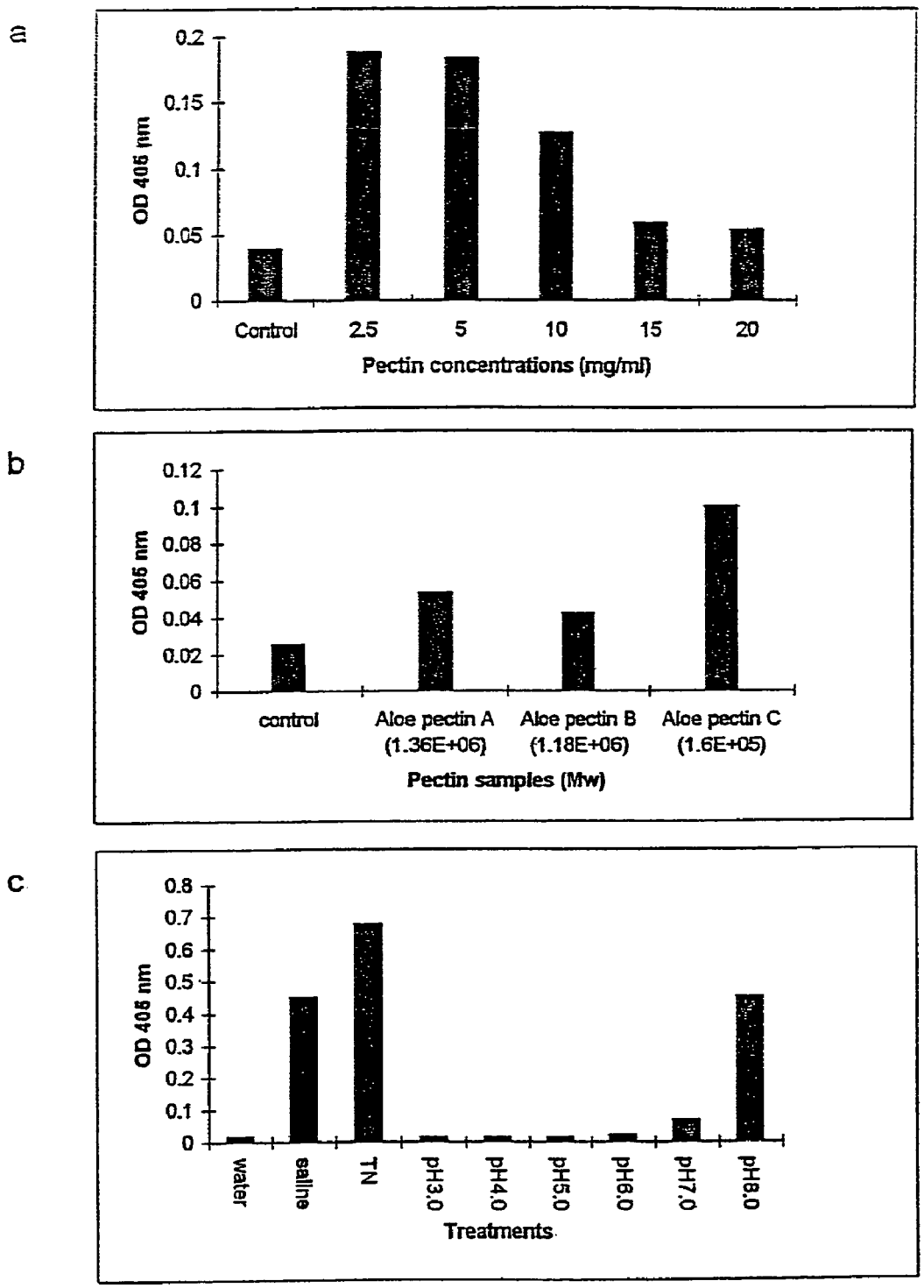
FIG. 5 shows the use of Aloe pectin as an encapsulating agent for controlled release. The relative amounts of the enzyme released from pectin beads were measured with substrate PNPP:
  (a) Spontaneous release in water in relation to pectin concentrations shown with APase-Ab conjugate beads;
  (b) Spontaneous release in water in relation to the sizes of Aloe pectins shown with APase-Ab conjugate beads made with 10 mg/ml Aloe pectins; and
  (c) Effect of pH and NaCl (150 mM) in triggering release shown with APase beads made with 15 mg/ml Aloe pectin ($1.36 \times 10^6$ Da). TN, 25 mM Tris and 150 mM NaCl, pH 7.4; saline, 150 mM NaCl.

The results showed that a pectin concentration above 10 mg/ml could efficiently inhibit the spontaneous release and pectins with larger sizes entrap the target agent more efficiently (FIGS. 5a and 5b). The conditions for triggering release were then examined. It was found that the entrapped enzymes were only released in saline (150 mM NaCl) or at a pH of 7.0 or above (FIG. 5c). The combination of these two conditions as represented by TN buffer (25 mM Tris, 150 mM NaCl, pH 7.4) gave the most efficient release (FIG. 5c).

Although the protein molecules used in the present experiments are large ones (APase, 140 kDa; APase-IgG, ~350 kDa), these results clearly indicate that there is a release mechanism in the Aloe pectin-calcium gel controlled by the salt concentration and pH. Thus, the physiological condition (150 mM NaCl and pH7.0–7.4) should initiate the release once the beads are delivered in vivo, whereas under the storage conditions no or only minimal release occurs. This Aloe pectin-calcium gel encapsulating system should be suitable for protein molecules such as antibodies and vaccines.

TABLE 14

Gel formation and degree of methylation (DM) of Aloe Pectin.

| | Aloe pectin | Citrus pectin | Citrus pectin | Polygalacturonic acid |
|---|---|---|---|---|
| Ca++ gel formation | Yes | Yes | NO | Yes |
| DM | LM (<50%) | LM (28%) | HM (64%) | 0 |

TABLE 15

Effect of endo-polygalacturonase on cold gelation of Aloe pectin in the presence of monovalent cation (NaCl).

| | Endo-polygalacturonase (unit/ml) | | | | |
|---|---|---|---|---|---|
| | 0 | 0.053 | 0.105 | 0.21 | 0.42 |
| Gel formation | Firm gel | Firm gel | Soft gel | Softer gel | Liquid |

EXAMPLE 15

Use of Monovalent Cation-Based Aloe Pectin Gel as A New Matrix for Antigen and Antibody Precipitation Reaction The precipitation assay is a common diagnostic method for detecting pathogen-specific antigens or antibodies. It involves carefully layering the antigen solution over the antibody solution or vice versa The layering step is important and care must be taken not to cause any disturbance between the two solutions. The formation of a white precipitation line between the two solutions as the result of diffusion indicates a positive result. Alternatively, this assay is performed in agar, which is referred as the agar diffusion assay. This assay involves preparation of agar and takes a longer time to see results.

The ability of HMW Aloe pectin to form a gel in PBS at 4° C. provides an opportunity to design a new, simpler assay. One solution is kept in the solid state at 4° C. so that another solution can be layered on top of it easily and consistently. When the gel is brought back to room temperature, it changes back to a non-viscous solution, allowing the diffusion to occur.

To test this potential usage, mouse IgG (antigen) and anti-mouse IgG antibodies (antibody) were used. 10 µl of the antigen at various concentrations was mixed with 0.4 ml of 1 mg/ml AP 97-1 in PBS. The tubes were then kept on ice and when a gel formed, 200 µl of the antibody solution in PBS was directly added onto the gel. The tubes were then returned to room temperature. After 30 min, a precipitation line appeared between the two solutions. When the antigen was added to the antibody solution with or without pectin at room temperature, no, or only diffused, precipitation lines were observed. This suggests that using the Aloe pectin gel as a matrix will not only simplify such antigen and antibody precipitation tests, but may also enhance their sensitivity.

EXAMPLE 16

Extraction by Supercritical Fluid

The cell wall fibers (as obtained in Example 3) are packed into the supercritical fluid (SF) extraction cell which is then sealed. The SF generator is turned on and upon reaching the desired conditions of temperature and pressure, the SF is pumped into the extraction cell at the appropriate flowrate. The pectin-rich exiting fluid is allowed to cool in the decompression chamber. The cooled fluid is then treated to isolate the pectin. One isolation method is to precipitate the pectin by the addition of a water-soluble organic solvent, preferably ethanol, to the fluid or partially evaporated fluid. The precipitated material is then separated by filtration or centrifugation and dried. The pectin can also be isolated from the fluid by removal of the fluid through freeze drying or evaporation. The fluid to be used for the SF extraction may be water or an aqueous solution containing an acid or a base or a buffer salt or a water-soluble organic modifier or any combination of the preceding additives. The process can be operated at temperatures between about 300° C. and about 800° C. and at pressures between about 200 atm. and about 1000 atm.

EXAMPLE 17

Extraction of Aloe Pectins with Enzymes

Cell wall fibers are washed with water and suspended at a proper concentration in a buffer permitting the maximum activity of the enzyme(s) to be used. The enzymes that can be used include endo-arabinase, endo-galactanase, and rhamnogalacturonase. The endo-polygalacturonase, while usable for the naturally HM pectins, is not suitable for Aloe pectin since it is a naturally LM one. The enzyme is then added. The fiber suspension is kept at 20–37° C. for certain period of time (1–24 hrs). Remaining fibers are removed by filtration. Pectins are precipitated with alcohol and dried.

EXAMPLE 18

Extraction of Aloe Pectins with Microbes

Cell wall fibers are washed with water and suspended in water at a proper concentration. Microbes, either bacteria or fingi, that produce enzymes capable of liberating pectins from cell walls, are added to the fiber suspension. *Bacillus subtilis* is one example of such bacteria. The enzymes produced include endo-arabinase, endo-galactanase, endo-polygalacturonase, and/or rhamnogalacturonase. The microbes producing mainly endo-polygalacturonase is avoided since the Aloe pectin is naturally LM pectin. The extraction lasts for certain period of time (5–24 hrs) at 20–37° C. The remaining fibers were removed by coarse filtration. The filtrate is then passed through a fine filter to remove the microbes. The final filtrate is mixed with alcohol (ethanol). The pectin precipitates are collected and dried.

EXAMPLE 19

Use of Monovalent Cation-Based Gel as a Storage Matrix for Pharmacological Agent Pharmacological agents are often stored in buffered or non-buffered physiological saline (0.15 M NaCl) at 0–8° C. A pharmacological agent is any material that exerts a physiological effect on a biological system, either an animal or a plant. One problem often encountered by this storage form is aggregate formation and precipitation over time.

The monovalent cation-based thermo-reversible gel of Aloe pectin can be formed under physiological conditions (0.15 M NaCl, pH 7.4) at low temperature (4° C.) with a very low pectin concentration (1 mg/ml). Incorporation of pharmacological agents in the gel would provide a matrix which would reduce the opportunity for aggregation. The monovalent cation-based gel quickly returns to solution once returned to RT (22° C.) so that the stored agent can be used in solution form.

The model protein bovine serum albumin (BSA) dissolved in physiological saline (0.15 M NaCl) was mixed with an equal volume of 2 mg/ml of Aloe pectin in 0.15 M NaCl. The final BSA concentration was 20 mg/ml and the final Aloe pectin concentration was 1 mg/mil. The mixture was then kept on ice. After ~15 min, a gel formed. This indicated that the monovalent cation-based gel has the capacity for high concentrations of biological agents.

Black india ink is made of tiny carbon particles that tend to precipitate over time when the suspension is left undisturbed. To demonstrate the ability of the monovalent cation-based gel to prevent precipitation, black india ink was introduced into the gel system. The black india ink (Higgins, Faber-Castell Corporation, NJ) was diluted 1000 times in 0.15 M NaCl. The diluted ink was the mixed with equal volumes of 2 mg/ml Aloe pectin in 0.15 M NaCl or with the 0.15 NaCl only as a control. The mixtures were placed on ice. The mixture with pectin quickly formed a gel and the control remained a solution. Both samples were then stored at 4° C. After 48 hrs, it was evident that the upper portion of the control solution was less dark as compared to the lower portion and a dense black area had formed at the bottom. This indicated that precipitation of the india ink particles had occurred. On the other hand, the gel was evenly dark and no dense black area was observed at the bottom of the tube. When the gel changed back to solution when returned to RT, the solution was also uniformly dark. This indicated that the gel could prevent the precipitation of the agents that may result from aggregation.

EXAMPLE 20

Physical and Chemical Characterization of Aloe Pectins

Appearance of the Final Products and Solutions The dried Aloe pectin derived from pulp fibers, had an off white appearance. This color was in sharp contrast to current commercial pectins of both citrus and apple including polygalacturonic acid prepared from citrus pectin, and other pectins currently being developed such as sunflower pectin. Both apple and sunflower pectins are tan and citrus pectins have a light yellow-brown color. The superior color quality of Aloe pectin from the pulp is likely due to the clear and color-free nature of the pulp.

When dissolved in water, the Aloe pectin solutions at a concentration of 5 mg/ml were essentially clear, whereas the commercial ones were cloudy to various extents with the apple pectins being the cloudiest. This observation was confirmed by measuring the absorbance at 600 nm (Table 16). The absorbance at 600 nm of Aloe pectins extracted from pulp fibers was at least 2 fold lower than any other pectins.

The Aloe pectins from green rind fibers exhibited a light green-brown powder color to an extent similar to that of citrus pectins. Its solution was less clear compared to the pulp pectins, but was as clear as the best citrus pectins (Table 16).

TABLE 16

The cloudiness of pectin solutions in water as measured at OD 600 nm.

| Source | Pectins (5 mg/ml in water) | OD 600 nm |
|---|---|---|
| Aloe pulp | AP 10679 | 0.028 |
|  | AP 97-1 | 0.044 |
| Aloe rind | AP rind B1 (RT) | 0.084 |
|  | AP rind B1-2 (HT) | 0.110 |
| Commercial | Citrus (LM), Sigma | 0.103 |
|  | Citrus (HM), Sigma | 0.082 |
|  | Citrus, Sigma | 0.176 |
|  | Citrus, Spectrum | 0.136 |
|  | Citrus, HF | 0.272 |
|  | Apple, HF | 0.345 |
|  | Polygalacuronic acid (citrus), Sigma | 0.206 | pectins are expected to be more flexible as compared to other pectins. This may give Aloe pectin some distinct rheological properties.

Aloe pectins also contained a rare sugar, 3-OMe-rhamnose (Table 7). It was detected in all samples including the purified AP 10679. It accounted for ~10% of the total rhamnose. The presence of this modified sugar has not been reported in any other pectins. The Aloe pectins of the present invention are relatively free of fiber. The fiber contents of the Aloe pectins so obtained are less than about 20% by weight, preferably less than about 5% by weight, and even more preferably less than about 1% by weight.

A summary of other properties of Aloe pectins extracted from crude pulp and rind fibers are given in Table 17.

While composition of isolated Aloe pectins and preferred methods for obtaining and using them have been disclosed, it will be apparent to those skilled in the art that numerous modifications and variations are possible in light of the above teaching. It should also be realized by those skilled in the art that such modifications and variations do not depart from the spirit and scope of the invention as set forth in the appended claims

TABLE 17

Overview of the properties of Aloe pectins extracted from crude pulp and rind fibers.

|  | Fiber source | Extraction temp. | Powder color | Solution clearness | MW | Intrinsic viscosity ($\eta$, ml/g) | Gal A content (%, w/w) | DM | DAc | Phenol (%, w/w) | Ca++ Gelation | Na+ Gelation |
|---|---|---|---|---|---|---|---|---|---|---|---|---|
| AP B16 | Pulp | RT | Off White | clear | $1.06 \times 10^6$ | 550 | 93 | 11 | ND* | <0.03 | + | + |
| AP B16-2 | Pulp | HT | Off White | clear | $6.08 \times 10^5$ | 337 | 92 | 18 | ND | <0.03 | + | ±† |
| AP 97-1 | Pulp | RT/HT | Off white | clear | $1.36 \times 10^6$ | 740 | 91 | 4.4 | 9.1 | <0.03 | + | + |
| AP rind B1 | Rind | RT | Light# brown | Cloudy# | ND | 978 | 81 | 4.0 | ND | 0.045 | + | + |
| AP rind B1-2 | Rind | HT | Light brown | cloudy | ND | 523 | 84 | 9.5 | ND | 0.041 | + | ± |
| AP rind B2 | Rind | RT | Light brown | cloudy | ND | 846 | 75 | ND | ND | 0.219 | + | + |

*Not determined.
†Soft gel.
The color and cloudiness can be significantly reduced by additional alcohol rinse.

Features Overview

When compared to other pectins, Aloe pectin exhibited some unique features. First, Aloe pectin had a much higher rhamnose content. This was shown with both unpurified and purified Aloe pectin in comparison to commercial pectins and experimental pectins reported in the literature (Tables 10 and 11). This was also shown when the extraction conditions were taken into consideration, i.e., Aloe pectin extracted with EDTA was compared to other pectins extracted in a similar manner (with a chelating agent) (Table 12). The rhamnose content in Aloe pectin is more than 3 fold higher in unpurified samples or more than 2 fold higher in purified samples compared to the corresponding forms of other pectins. This difference was further substantiated by the fact that rhamnose/Gal A ratios in Aloe pectin were similarly higher. Rhamnose, being a backbone sugar, has a critical effect on the backbone chain flexibility; the more rhamnose present, the more flexible the molecule will be. Thus, Aloe

What is claimed is:

1. A composition for the sustained release of a pharmacological agent comprising:
    at least one pharmacological agent; and
    a pectin having a degree of methylation of less than 10% and an average molecular weight higher than $1 \times 10^6$ Daltons.

2. The composition of claim 1 further comprising a carrier.

3. The composition of claim 2 wherein the carrier comprises water, saline, buffered aqueous solution, emulsion, or adjuvant.

4. The composition of claim 1, wherein the pectin is a polygalacturonic acid.

5. The composition of claim 1, wherein the pectin is an Aloe pectin.

6. The composition of claim 1, wherein the concentration of the pectin is from about 0.5 mg/ml to about 40 mg/ml.

7. The composition of claim 1 wherein the pectin, when dissolved in 0.1 M NaCl at a concentration of 0.0005–0.2% (w/v), has an intrinsic viscosity greater than 550 ml/g.

8. The composition of claim 1 wherein the pectin has a galacturonic acid content of greater than 70% by weight.

9. The composition of claim 1 wherein the pectin has a rhamnose content from about 3% to about 15% by mole.

10. The composition of claim 1 wherein the pectin has a galacturonic acid content of greater than 70% by weight and a rhamnose content from about 3% to about 6% by mole.

11. The composition of claim 1 wherein the pectin comprises 3-OMe Rhamnose at greater than about 0.1% by mole.

12. The composition of claim 1 wherein the pharmacological agent is a protein.

13. The composition of claim 1 wherein the pharmacological agent is a vaccine.

14. The composition of claim 1 wherein the pharmacological agent is an antigen or antibody.

15. The composition of claim 1 further comprising calcium cations.

16. The composition of claim 15 in the form of a bead that encapsulates the pharmacological agent.

17. The composition of claim 1 further comprising an aqueous carrier, wherein the pectin is dissolved in the aqueous carrier to form a first solution, and wherein the pectin is present in an amount sufficient to form gel beads by dropping the first solution into a second solution comprising calcium cations.

18. The composition of claim 1 further comprising an aqueous carrier, wherein the pectin is dissolved in the aqueous carrier to form a solution, and wherein the pectin is present at a concentration from about 10 mg/ml to about 15 mg/ml.

19. The composition of claim 1 further comprising an aqueous carrier, wherein the pectin is dissolved in the aqueous carrier to form a solution, and wherein the pectin is present at a concentration from about 1 mg/ml and about 5 mg/ml.

20. The composition of claim 1 further comprising an aqueous carrier and a monovalent cation salt, in the form of a solution.

21. The composition of claim 20 wherein the pectin is present at a concentration from about 1 mg/ml and about 5 mg/ml.

22. The composition of claim 20 in the form of a gel.

23. The composition of claim 20 wherein the monovalent cation salt is a sodium salt, and the composition does not comprise a divalent cation salt.

24. The composition of claim 23 in the form of a gel.

25. The composition of claim 1 wherein the pectin has a rhamnose content from about 2% to about 15% by mole.

26. A composition for the sustained release of a pharmacological agent comprising:
 at least one pharmacological agent; and
 a pectin having a degree of methylation of about 17.5% or less and an average molecular weight about $6.08 \times 10^5$ Daltons or higher.

* * * * *

UNITED STATES PATENT AND TRADEMARK OFFICE
CERTIFICATE OF CORRECTION

PATENT NO.       : 7,022,683 B1                           Page 1 of 4
APPLICATION NO.  : 09/325610
DATED            : April 4, 2006
INVENTOR(S)      : Ni et al.

It is certified that error appears in the above-identified patent and that said Letters Patent is hereby corrected as shown below:

On Title page, under item (56) "References Cited," "U.S. Patent Documents," please insert the following:

| | | |
|---|---|---|
| --US 4,199,560 | 04/22/1980 | Gyarmati et al. |
| US 4,305,933 | 12/15/1981 | Wiczer |
| US 4,500,510 | 02/19/1985 | Goldstein |
| US 4,613,500 | 09/23/1986 | Suzuki et al. |
| US 4,652,441 | 03/24/1987 | Okada et al. |
| US 4,711,782 | 12/08/1987 | Okada et al. |
| US 4,725,438 | 02/16/1988 | Leazer |
| US 4,847,091 | 07/11/1989 | Illum |
| US 4,842,866 | 06/27/1989 | Horder et al. |
| US 4,891,226 | 01/02/1990 | Bremecker et al. |
| US 4,917,890 | 04/17/1990 | McAnalley |
| US 4,917,893 | 04/17/1990 | Okada et al. |
| US 4,925,677 | 05/15/1990 | Feijen |
| US 4,981,875 | 01/01/1991 | Leusner et al. |
| US 5,059,189 | 10/22/1991 | Cilento et al. |
| US 5,061,492 | 10/29/1991 | Okada et al. |
| US 5,064,650 | 11/12/1991 | Lew |
| US 5,079,018 | 01/07/1992 | Ecanow |
| US 5,188,825 | 02/23/1993 | Iles et al. |
| US 5,192,802 | 03/09/1993 | Rencher |
| US 5,204,108 | 04/20/1993 | Illum |
| US 5,208,031 | 05/04/1993 | Kelly |
| US 5,266,318 | 11/30/1993 | Taylor-McCord |
| US 5,284,659 | 02/08/1994 | Cherukuri et al |
| US 5,288,500 | 02/22/1994 | Ibsen |
| US 5,314,915 | 05/24/1994 | Rencher |
| US 5,362,424 | 11/08/1994 | Lee et al. |
| US 5,409,703 | 04/25/1995 | McAnnalley et al. |
| US 5,435,997 | 07/25/1995 | Burns |
| US 5,503,822 | 04/02/1996 | Schulman |
| US 5,508,043 | 04/16/1996 | Krishnamurthy |
| US 5,512,306 | 04/30/1996 | Carlsson et al. |
| US 5,525,634 | 06/11/1996 | Sintov et al. |
| US 5,545,673 | 08/13/1996 | Kelly |
| US 5,571,531 | 11/05/1996 | McDermott et al. |
| US 5,578,307 | 11/26/1996 | Wunderlich et al. |
| US 5,599,551 | 02/04/1997 | Kelly |

UNITED STATES PATENT AND TRADEMARK OFFICE
CERTIFICATE OF CORRECTION

PATENT NO. : 7,022,683 B1
APPLICATION NO. : 09/325610
DATED : April 4, 2006
INVENTOR(S) : Ni et al.

It is certified that error appears in the above-identified patent and that said Letters Patent is hereby corrected as shown below:

On Title page, under Item (56) "References Cited," (*continued*):

| | | |
|---|---|---|
| US 5,612,053 | 03/18/1997 | Baichwal *et al.* |
| US 5,622,717 | 04/22/1997 | Fuisz |
| US 5,639,795 | 06/17/1997 | Friedman *et al.* |
| US 5,645,827 | 07/08/1997 | Marlin *et al.* |
| US 5,648,399 | 07/15/1997 | Friedman *et al.* |
| US 5,651,987 | 07/29/1997 | Fuisz |
| US 5,674,495 | 10/07/1997 | Bowersock *et al.* |
| US 5,690,954 | 11/25/1997 | Illum |
| US 5,707,644 | 01/13/1998 | Illum |
| US 5,738,865 | 04/14/1998 | Baichwal *et al.* |
| US 5,760,102 | 06/02/1998 | Hall *et al.* |
| US 5,770,582 | 06/23/1998 | von Borstel *et al.* |
| US 5,804,212 | 09/08/1998 | Illum |
| US 5,811,123 | 09/22/1998 | Fuisz |
| US 5,840,332 | 11/24/1998 | Lerner *et al.* |
| US 5,863,554 | 01/26/1999 | Illum |
| US 5,900,238 | 05/04/1999 | Gombotz *et al.* |
| US 5,902,796 | 05/11/1999 | Shand *et al.* |
| US 5,935,604 | 08/10/1999 | Illum |
| US 6,033,651 | 03/07/2000 | Dolak *et al.* |
| US 6,060,078 | 05/09/2000 | Lee |
| US 6,063,915 | 05/16/2000 | Hansen *et al.* |
| US 6,083,531 | 07/04/2000 | Humbert-Droz *et al.* |
| US 6,103,269 | 08/15/2000 | Wunderlich *et al.* |
| US 6,133,440 | 10/17/2000 | Qiu *et al.* |
| US 6,136,334 | 10/24/2000 | Viegas *et al.* |
| US 6,139,880 | 10/31/2000 | Dolak *et al.* |
| US 6,149,940 | 11/21/2000 | Maggi *et al.* |
| US 6,159,491 | 12/12/2000 | Durrani |
| US 6,174,549 | 01/16/2001 | Greenshields *et al.* |
| US 6,197,327 | 03/06/2001 | Harrison *et al.* |
| US 6,197,346 | 03/06/2001 | Mathiowitz *et al.* |
| US 6,210,710 | 04/03/2001 | Skinner |
| US 6,217,908 | 04/17/2001 | Mathiowitz *et al.* |
| US 6,228,387 | 05/08/2001 | Borod |
| US 6,228,396 | 05/08/2001 | Watts |
| US 6,231,888 | 05/15/2001 | Lerner *et al.* |
| US 6,248,360 | 06/19/2001 | Choi *et al.* |
| US 6,261,574 | 07/17/2001 | Costello |

UNITED STATES PATENT AND TRADEMARK OFFICE
CERTIFICATE OF CORRECTION

PATENT NO.       : 7,022,683 B1
APPLICATION NO.  : 09/325610
DATED            : April 4, 2006
INVENTOR(S)      : Ni et al.

It is certified that error appears in the above-identified patent and that said Letters Patent is hereby corrected as shown below:

On Title page, under Item (56) "References Cited," (*continued*):

| | | |
|---|---|---|
| US 6,274,548 | 08/14/2001 | Ni *et al.* |
| US 6,284,273 | 09/04/2001 | Lenaerts *et al.* |
| US 6,290,964 | 09/18/2001 | Shupe *et al.* |
| US 6,309,675 | 10/30/2001 | Sobczak |
| US 6,310,089 | 10/30/2001 | Watts *et al.* |
| US 6,333,194 | 12/25/2001 | Levy *et al.* |
| US 6,342,251 | 01/29/2002 | Illum *et al.* |
| US 6,350,469 | 02/26/2002 | Daggy *et al* |
| US 6,355,276 | 03/12/2002 | Illum *et al.* |
| US 6,358,525 | 03/19/2002 | Guo *et al.* |
| US 6,365,200 | 04/02/2002 | Birnholz *et al.* |
| US 6,365,624 | 04/02/2002 | Davidson *et al.* |
| US 6,368,639 | 04/09/2002 | Farooqui *et al.* |
| US 6,375,963 | 04/23/2002 | Repka *et al.* |
| US 6,375,988 | 04/23/2002 | Suzuki *et al.* |
| US 6,383,495 | 05/07/2002 | Ramakrishna *et al.* |
| US 6,383,513 | 05/07/2002 | Watts *et al.* |
| US 6,387,394 | 05/14/2002 | Baichwal *et al.* |
| US 6,387,408 | 05/14/2002 | Illum *et al.* |
| US 6,387,917 | 05/14/2002 | Illum *et al.* |
| US 6,391,318 | 05/21/2002 | Illum *et al.* |
| US 6,413,494 | 07/02/2002 | Lee *et al.* |
| US 6,413,941 | 07/02/2002 | Garnett *et al.* |
| US 6,416,779 | 07/09/2002 | D'Augustine *et al.* |
| US 6,423,345 | 07/23/2002 | Bernstein *et al.* |
| US 6,451,351 | 09/17/2002 | Kawashima *et al.* |
| US 6,455,066 | 09/24/2002 | Fischer *et al.* |
| US 6,465,626 | 10/15/2002 | Watts |
| US 6,475,526 | 11/05/2002 | Smith |
| US 6,517,868 | 02/11/2003 | Fassihi *et al.* |
| US 6,531,152 | 03/11/2003 | Lerner *et al.* |
| US 6,534,065 | 03/18/2003 | Makin *et al.* |
| US 6,541,035 | 04/01/2003 | Pallado *et al.* |
| US 6,551,631 | 04/22/2003 | Shupe *et al.* |
| US 6,552,024 | 04/22/2003 | Chen *et al.* |
| US 6,562,363 | 05/13/2003 | Mantelle *et al.* |
| US 6,569,463 | 05/27/2003 | Patel *et al.* |
| US 6,596,297 | 07/22/2003 | Neurath *et al.* |
| US 6,632,457 | 10/14/2003 | Sawhney |

UNITED STATES PATENT AND TRADEMARK OFFICE
CERTIFICATE OF CORRECTION

PATENT NO.       : 7,022,683 B1
APPLICATION NO.  : 09/325610
DATED            : April 4, 2006
INVENTOR(S)      : Ni et al.

It is certified that error appears in the above-identified patent and that said Letters Patent is hereby corrected as shown below:

On Title page, under Item (56) "References Cited," (*continued*):

| | | |
|---|---|---|
| US 6,824,790 | 11/30/2004 | Yatvin |
| US 2001/0043949 | 11/22/2001 | Delgado |
| US 2001/0046518 | 11/29/2001 | Sawhney |
| US 2001/0046519 | 11/29/2001 | Illum *et al.* |
| US 2001/0051613 | 12/13/2001 | Illum *et al.* |
| US 2001/0053359 | 12/20/2001 | Watts *et al.* |
| US 2001/0055569 | 12/27/2001 | Davis *et al.* |
| US 2002/0001610 | 01/03/2002 | Cohen *et al.* |
| US 2002/0001619 | 01/02/2002 | Goldenberg *et al.* |
| US 2002/0009438 | 01/24/2002 | Shupe *et al.* |
| US 2002/0044972 | 04/18/2002 | Davis *et al.* |
| US 2002/0068091 | 06/06/2002 | Davis *et al.* |
| US 2002/0098198 | 07/25/2002 | Watts *et al.* |
| US 2002/0197324 | 12/26/2002 | Watts *et al.* |
| US 2003/0039665 | 02/27/2003 | Illum *et al.* |
| US 2003/0059440 | 03/27/2003 | Clarot *et al.* |
| US 2003/0060486 | 03/27/2003 | Jacob *et al.* |
| US 2003/0068376 | 04/10/2003 | Chen *et al.* |
| US 2003/0068378 | 04/10/2003 | Chen *et al.* |
| US 2003/0077296 | 04/24/2003 | Denton *et al.* |
| US 2003/0118653 | 06/26/2003 | Chen *et al.* |
| US 2003/0138505 | 07/24/2003 | Fischer *et al.* |
| US 2003/0143274 | 07/31/2003 | Viegas *et al.* |
| US 2003/0152629 | 08/14/2003 | Shefer *et al.*-- |

Signed and Sealed this

Tenth Day of October, 2006

JON W. DUDAS
*Director of the United States Patent and Trademark Office*